(12) United States Patent
Scheller et al.

(10) Patent No.: US 9,375,351 B2
(45) Date of Patent: *Jun. 28, 2016

(54) STEERABLE LASER PROBE

(71) Applicant: Katalyst Surgical, LLC, Chesterfield, MO (US)

(72) Inventors: Gregg D Scheller, Wildwood, MO (US); Matthew N Zeid, Ballwin, MO (US); Justin M Raney, O'Fallon, MO (US)

(73) Assignee: Katalyst Surgical, LLC, Chesterfield, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/955,761

(22) Filed: Dec. 1, 2015

(65) Prior Publication Data

US 2016/0120698 A1   May 5, 2016

Related U.S. Application Data

(63) Continuation of application No. 14/533,180, filed on Nov. 5, 2014, now Pat. No. 9,320,649.

(51) Int. Cl.
*A61B 18/18* (2006.01)
*A61F 9/008* (2006.01)
(Continued)

(52) U.S. Cl.
CPC ....... *A61F 9/00821* (2013.01); *A61B 17/00234* (2013.01); *A61B 18/20* (2013.01); *A61B 2017/00305* (2013.01); *A61B 2017/00336* (2013.01); *A61B 2018/0091* (2013.01); *A61B 2018/00184* (2013.01); *A61B 2018/00589* (2013.01)

(58) Field of Classification Search
CPC .............. A61B 17/00234; A61B 18/20; A61F 9/00821
USPC ........................................................... 606/4
See application file for complete search history.

(56) References Cited

U.S. PATENT DOCUMENTS 5,190,050 A    3/1993  Nitzsche
5,355,871 A    10/1994 Hurley et al.
(Continued)

FOREIGN PATENT DOCUMENTS

EP           0900547 B1      3/1999
NL    WO 2013/133717        9/2013
WO    WO 2006/091597 A1    8/2006

OTHER PUBLICATIONS

H. Fischer, B. Vogel, W. Pfleging, H. Besser, Flexible distal tip made of nitinol (NiTi) for a steerable endoscopic camera system, Materials Science and Engineering A273-275 (1999) 780-783.

*Primary Examiner* — Lynsey Crandall
*Assistant Examiner* — Sebastian X Lukjan
(74) *Attorney, Agent, or Firm* — Kevin P. Rollins

(57) ABSTRACT

A steerable laser probe may include a handle having a handle distal end and a handle proximal end, an actuation control of the handle, a flexible housing tube having a flexible housing tube distal end and a flexible housing tube proximal end, an optic fiber disposed within an inner portion of the handle and the flexible housing tube, and a cable disposed within the flexible housing tube and the actuation control. A rotation of the actuation control may be configured to gradually curve the flexible housing tube and the optic fiber. A rotation of the actuation control may be configured to gradually straighten the flexible housing tube and the optic fiber.

18 Claims, 15 Drawing Sheets

(51) Int. Cl.
*A61B 18/20* (2006.01)
*A61B 17/00* (2006.01)
*A61B 18/00* (2006.01)

(56) References Cited

U.S. PATENT DOCUMENTS

| | | | |
|---|---|---|---|
| 5,381,782 | A | 1/1995 | DeLaRama et al. |
| 5,439,000 | A | 8/1995 | Gunderson et al. |
| 5,454,794 | A | 10/1995 | Narciso et al. |
| 5,520,222 | A | 5/1996 | Chikama |
| 5,855,577 | A | 1/1999 | Murphy-Chutorian et al. |
| 6,123,699 | A | 9/2000 | Webster, Jr. |
| 6,126,654 | A | 10/2000 | Giba et al. |
| 6,178,354 | B1 | 1/2001 | Gibson |
| 6,198,974 | B1 | 3/2001 | Webster, Jr. |
| 6,488,695 | B1 | 12/2002 | Hickingbotham |
| 6,505,530 | B2 | 1/2003 | Adler et al. |
| 6,530,913 | B1 | 3/2003 | Giba et al. |
| 6,533,772 | B1 | 3/2003 | Sherts et al. |
| 6,551,302 | B1 | 4/2003 | Rosinko et al. |
| 6,572,608 | B1 | 6/2003 | Lee et al. |
| 6,620,153 | B2 | 9/2003 | Mueller et al. |
| 6,730,076 | B2 | 5/2004 | Hickingbotham |
| 6,863,668 | B2 | 3/2005 | Gillespie et al. |
| 6,984,230 | B2 | 1/2006 | Scheller et al. |
| 7,004,957 | B1 | 2/2006 | Dampney et al. |
| 7,303,533 | B2 | 12/2007 | Johansen et al. |
| 7,402,158 | B2 | 7/2008 | Scheller et al. |
| 7,632,242 | B2 | 12/2009 | Griffin et al. |
| 7,766,904 | B2 | 8/2010 | Mc Gowan, Sr. et al. |
| 8,038,692 | B2 | 10/2011 | Valencia et al. |
| 8,075,553 | B2 | 12/2011 | Scheller et al. |
| 8,197,468 | B2 | 6/2012 | Scheller et al. |
| 8,840,605 | B2 | 9/2014 | Scheller et al. |
| 8,840,607 | B2 | 9/2014 | Scheller et al. |
| 8,951,245 | B2 | 2/2015 | Scheller et al. |
| 8,968,277 | B2 | 3/2015 | Scheller et al. |
| 9,023,019 | B2 | 5/2015 | Scheller et al. |
| 9,023,020 | B2 | 5/2015 | Scheller et al. |
| 9,039,686 | B2 | 5/2015 | Scheller et al. |
| 9,089,399 | B2 | 7/2015 | Scheller et al. |
| 9,107,682 | B2 | 8/2015 | Scheller et al. |
| 9,113,995 | B2 | 8/2015 | Scheller et al. |
| 9,119,702 | B2 | 9/2015 | Scheller et al. |
| 2003/0171762 | A1 | 9/2003 | Forchette et al. |
| 2004/0181138 | A1 | 9/2004 | Hindricks et al. |
| 2004/0249367 | A1 | 12/2004 | Saadat et al. |
| 2005/0054900 | A1 | 3/2005 | Mawn et al. |
| 2005/0157985 | A1 | 7/2005 | McGowan, Sr. et al. |
| 2005/0234437 | A1 | 10/2005 | Baxter et al. |
| 2005/0272975 | A1 | 12/2005 | McWeeney et al. |
| 2005/0277874 | A1 | 12/2005 | Selkee |
| 2006/0129175 | A1 | 6/2006 | Griffin et al. |
| 2006/0178674 | A1 | 8/2006 | McIntyre |
| 2007/0185514 | A1 | 8/2007 | Kirchhevel |
| 2007/0260231 | A1 | 11/2007 | Rose et al. |
| 2008/0132761 | A1 | 6/2008 | Sonnenschein et al. |
| 2009/0018393 | A1 | 1/2009 | Dick et al. |
| 2009/0163943 | A1 | 6/2009 | Cavanaugh et al. |
| 2009/0187170 | A1 | 7/2009 | Auld et al. |
| 2009/0312750 | A1 | 12/2009 | Spaide |
| 2010/0004642 | A1 | 1/2010 | Lumpkin |
| 2010/0191224 | A1 | 7/2010 | Butcher |
| 2010/0268234 | A1 | 10/2010 | Aho et al. |
| 2011/0028947 | A1 | 2/2011 | Scheller et al. |
| 2012/0116361 | A1 | 5/2012 | Hanlon et al. |
| 2012/0245569 | A1 | 9/2012 | Papac et al. |
| 2013/0035551 | A1 | 2/2013 | Yu et al. |
| 2013/0060240 | A1 | 3/2013 | Scheller et al. |
| 2013/0071507 | A1 | 3/2013 | Scheller et al. |
| 2013/0090635 | A1 | 4/2013 | Mansour |
| 2013/0096541 | A1 | 4/2013 | Scheller et al. |
| 2013/0116671 | A1 | 5/2013 | Scheller et al. |
| 2013/0150838 | A1 | 6/2013 | Scheller et al. |
| 2013/0165910 | A1 | 6/2013 | Scheller et al. |
| 2013/0261610 | A1 | 10/2013 | Laconte et al. |
| 2013/0281994 | A1 | 10/2013 | Scheller et al. |
| 2013/0304043 | A1 | 11/2013 | Scheller et al. |
| 2013/0304048 | A1 | 11/2013 | Scheller et al. |
| 2014/0005642 | A1 | 1/2014 | Scheller et al. |
| 2014/0039471 | A1 | 2/2014 | Scheller et al. |
| 2014/0039472 | A1 | 2/2014 | Scheller et al. |
| 2014/0039475 | A1 | 2/2014 | Scheller et al. |
| 2014/0046307 | A1 | 2/2014 | Scheller et al. |
| 2014/0052115 | A1 | 2/2014 | Zeid et al. |
| 2014/0066907 | A1 | 3/2014 | Scheller et al. |
| 2014/0066912 | A1 | 3/2014 | Scheller et al. |
| 2014/0074073 | A1 | 3/2014 | Scheller et al. |
| 2014/0074079 | A1 | 3/2014 | Scheller et al. |
| 2014/0088572 | A1 | 3/2014 | Scheller et al. |
| 2014/0088576 | A1 | 3/2014 | Scheller et al. |
| 2014/0107628 | A1 | 4/2014 | Scheller et al. |
| 2014/0107629 | A1 | 4/2014 | Scheller et al. |
| 2015/0038950 | A1 | 2/2015 | Scheller et al. |

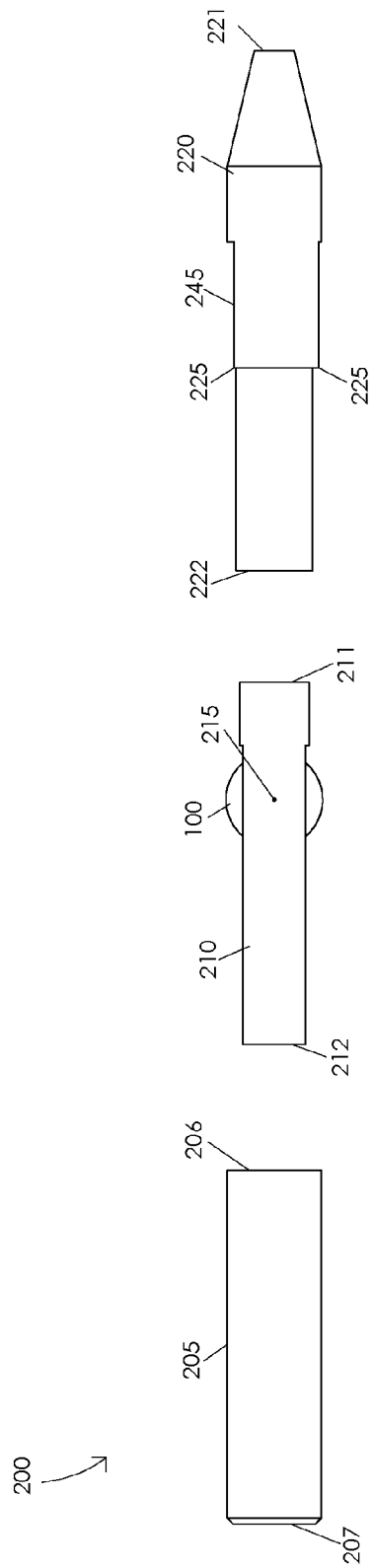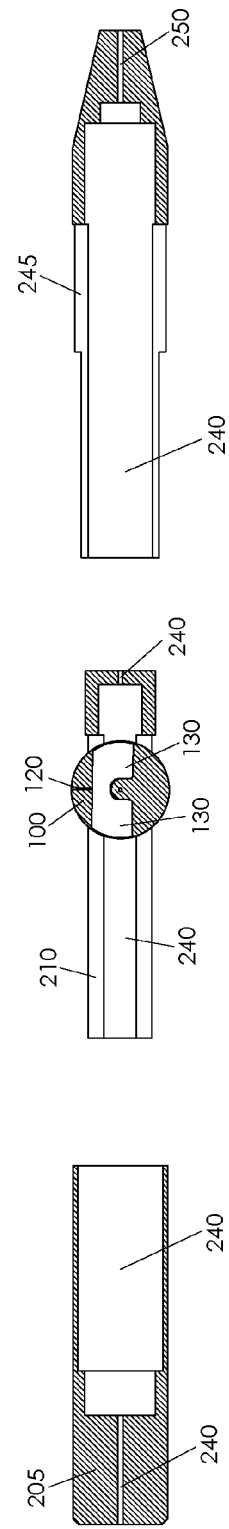
FIG. 2A
FIG. 2B

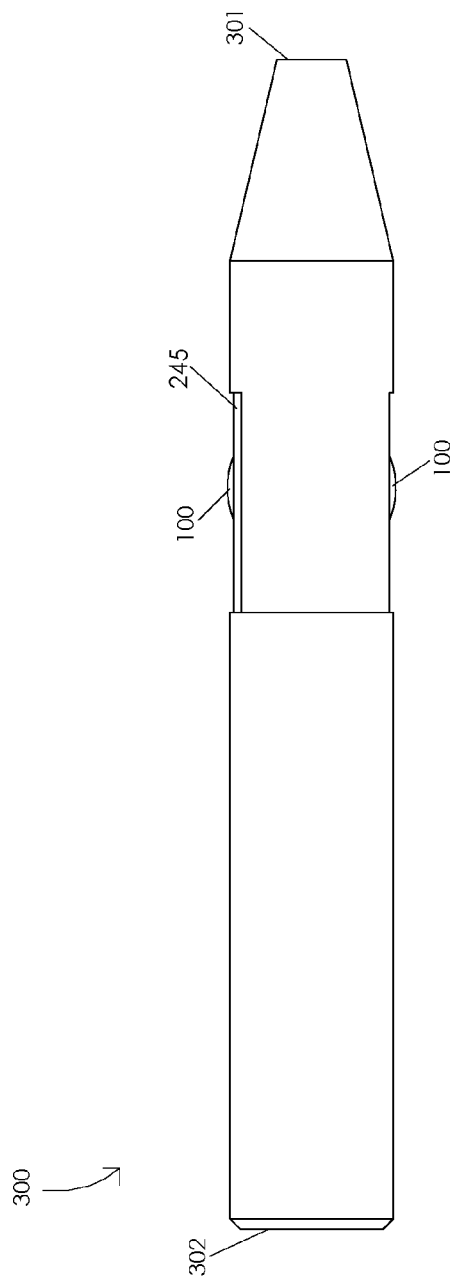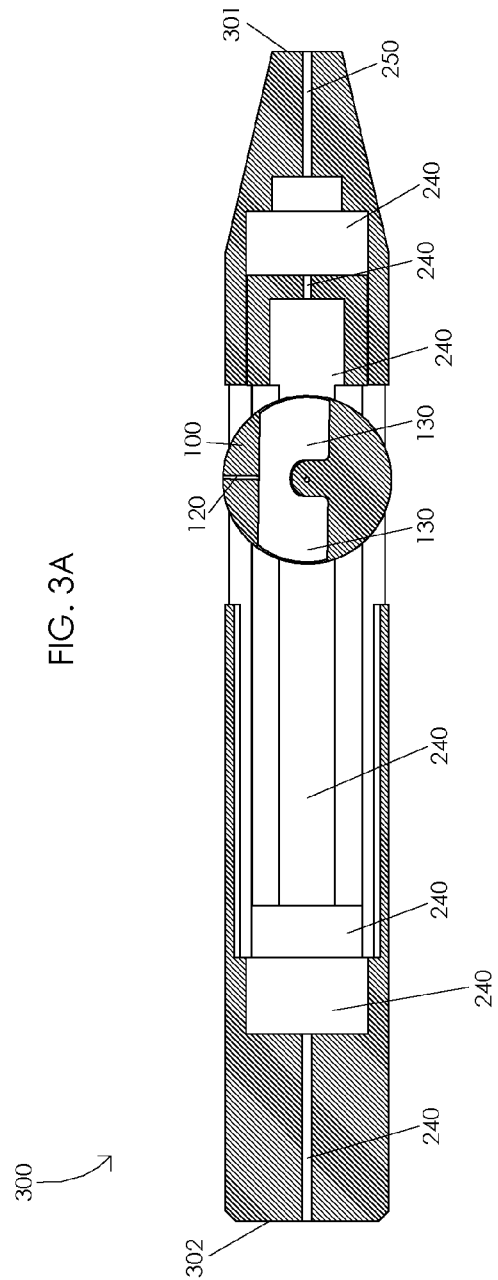

STEERABLE LASER PROBE

CROSS-REFERENCE TO RELATED APPLICATIONS

This application is a continuation of prior application Ser. No. 14/533,180 filed Nov. 5, 2014.

FIELD OF THE INVENTION

The present disclosure relates to a surgical instrument, and, more particularly, to a steerable laser probe.

BACKGROUND OF THE INVENTION

A wide variety of ophthalmic procedures require a laser energy source. For example, ophthalmic surgeons may use laser photocoagulation to treat proliferative retinopathy. Proliferative retinopathy is a condition characterized by the development of abnormal blood vessels in the retina that grow into the vitreous humor. Ophthalmic surgeons may treat this condition by energizing a laser to cauterize portions of the retina to prevent the abnormal blood vessels from growing and hemorrhaging.

In order to increase the chances of a successful laser photocoagulation procedure, it is important that a surgeon is able aim the laser at a plurality of targets within the eye, e.g., by guiding or moving the laser from a first target to a second target within the eye. It is also important that the surgeon is able to easily control a movement of the laser. For example, the surgeon must be able to easily direct a laser beam by steering the beam to a first position aimed at a first target, guide the laser beam from the first position to a second position aimed at a second target, and hold the laser beam in the second position. Accordingly, there is a need for a surgical laser probe that can be easily guided to a plurality of targets within the eye.

BRIEF SUMMARY OF THE INVENTION

The present disclosure presents a steerable laser probe. In one or more embodiments, a steerable laser probe may comprise a handle having a handle distal end and a handle proximal end, an actuation control of the handle, a flexible housing tube having a flexible housing tube distal end and a flexible housing tube proximal end, an optic fiber disposed within an inner portion of the handle and the flexible housing tube, and a cable disposed within the flexible housing tube and the actuation control. Illustratively, a rotation of the actuation control may be configured to gradually curve the flexible housing tube. In one or more embodiments, a gradual curving of the flexible housing tube may be configured to gradually curve the optic fiber. Illustratively, a rotation of the actuation control may be configured to gradually straighten the flexible housing tube. In one or more embodiments, a gradual straightening of the flexible housing tube may be configured to gradually straighten the optic fiber.

BRIEF DESCRIPTION OF THE DRAWINGS

The above and further advantages of the present invention may be better understood by referring to the following description in conjunction with the accompanying drawings in which reference numerals indicate identical or functionally similar elements:

FIGS. 2A and 2B are schematic diagrams illustrating an exploded view of a handle assembly;

FIGS. 3A and 3B are schematic diagrams illustrating a handle;

DETAILED DESCRIPTION OF AN ILLUSTRATIVE EMBODIMENT

Figure 1A:
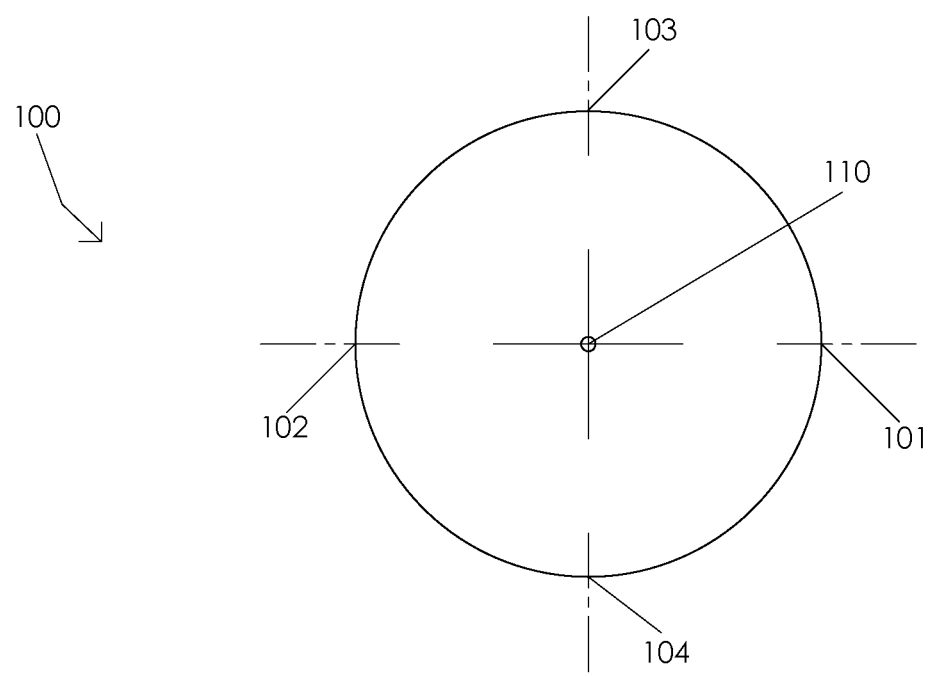
FIGS. 1A and 1B are schematic diagrams illustrating an actuation control.
Figure 1B:
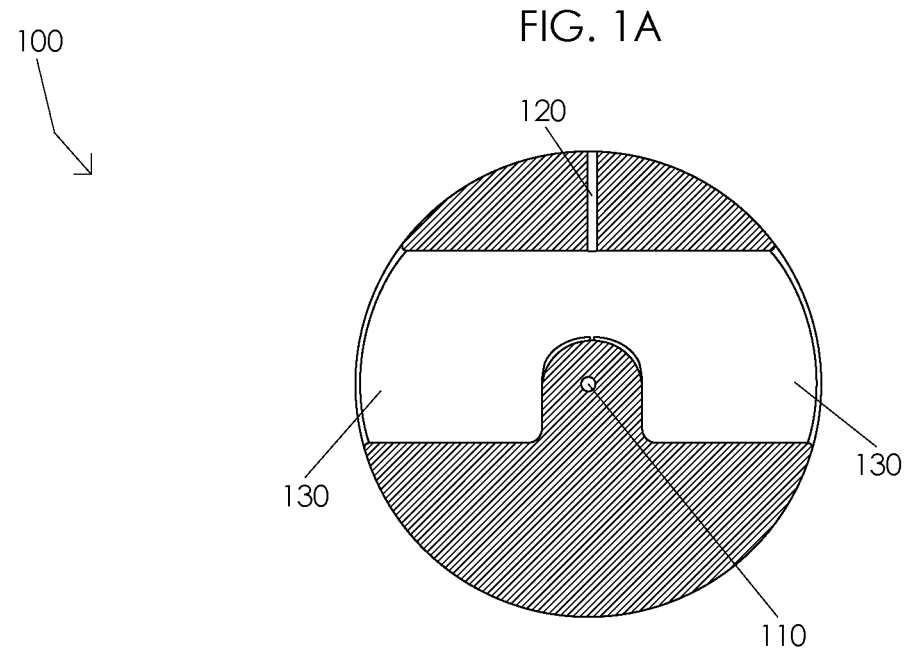

FIGS. 1A and 1B are schematic diagrams illustrating an actuation control 100. FIG. 1A illustrates a side view of an actuation control 100. Illustratively, actuation control 100 may comprise an actuation control distal end 101, an actuation control proximal end 102, an actuation control anterior end 103, and an actuation control posterior end 104. FIG. 1B illustrates a cross-sectional view of an actuation control 100. In one or more embodiments, actuation control 100 may comprise a fixation pin guide 110, a cable housing 120, and an actuation chamber 130. Illustratively, actuation control 100 may be manufactured from any suitable material, e.g., polymers, metals, metal alloys, etc., or from any combination of suitable materials.

FIGS. 2A and 2B are schematic diagrams illustrating an exploded view of a handle assembly 200. FIG. 2A illustrates a side view of a handle assembly 200. In one or more embodiments, handle assembly 200 may comprise a handle end cap 205 having a handle end cap distal end 206 and a handle end cap proximal end 207, an actuation control mount 210 having an actuation control mount distal end 211 and an actuation control mount proximal end 212, an actuation control 100, a fixation pin 215, a handle base 220 having a handle base distal end 221 and a handle base proximal end 222, and a handle end cap interface 225. Illustratively, actuation control 100 may be disposed within actuation control mount 210. In one or more embodiments, fixation pin 215 may be configured to fix actuation control 100 within actuation control mount 210, e.g., fixation pin 215 may be disposed within a portion of actuation control mount 210 and within a portion of actuation control 100. Illustratively, fixation pin 215 may be disposed within actuation control mount 210 and fixation pin guide 110. In one or more embodiments, actuation control 100 may be rotated about fixation pin 215, e.g., a surgeon may rotate actuation control 100 within actuation control mount 210 by applying a force to a portion of actuation control 100.

FIG. 2B illustrates a cross-sectional view of a handle assembly 200. Illustratively, handle assembly 200 may comprise a handle inner portion 240, an auto-fixing component housing 245, and a flexible housing tube housing 250. In one or more embodiments, actuation control 100 may be oriented wherein a portion of actuation chamber 130 may be disposed within a portion of handle inner portion 240. Illustratively, handle end cap 205, actuation control mount 210, and handle base 220 may be manufactured from any suitable material, e.g., polymers, metals, metal alloys, etc., or from any combination of suitable materials.

FIGS. 3A and 3B are schematic diagrams illustrating a handle 300. FIG. 3A illustrates a side view of a handle 300. Illustratively, handle 300 may comprise a handle distal end 301 and a handle proximal end 302. In one or more embodiments, handle distal end 301 may comprise a portion of handle base 220, e.g., handle distal end 301 may comprise handle base distal end 221. Illustratively, handle proximal end 302 may comprise a portion of end cap 205, e.g., handle proximal end 302 may comprise handle end cap proximal end 207.

FIG. 3B illustrates a cross-sectional view of a handle 300. In one or more embodiments, actuation control mount 210 may be disposed within handle end cap 205 and handle base 220. Illustratively, actuation control mount 210 may be disposed within handle end cap 205 and handle base 220 wherein a portion of actuation control 100 may be adjacent to a portion of auto-fixing component housing 245. In one or more embodiments, a portion of handle base 220 may be disposed within a portion of handle end cap 205, e.g., handle base proximal end 222 may be disposed within handle end cap 205. In one or more embodiments, a portion of handle base 220 may be disposed within handle end cap 205 wherein handle end cap interface 225 may be configured to interface with a portion of handle end cap 205, e.g., handle end cap interface 225 may be configured to interface with handle end cap distal end 206. Illustratively, a portion of handle base 220 may be fixed within handle end cap 205, e.g., by an adhesive or any suitable fixation means. In one or more embodiments, a portion of handle base 220 may be fixed within handle end cap 205 by a press fit, a setscrew, a weld, etc. Illustratively, handle base 220 and handle end cap 205 may be manufactured as a single unit.

Figure 4:
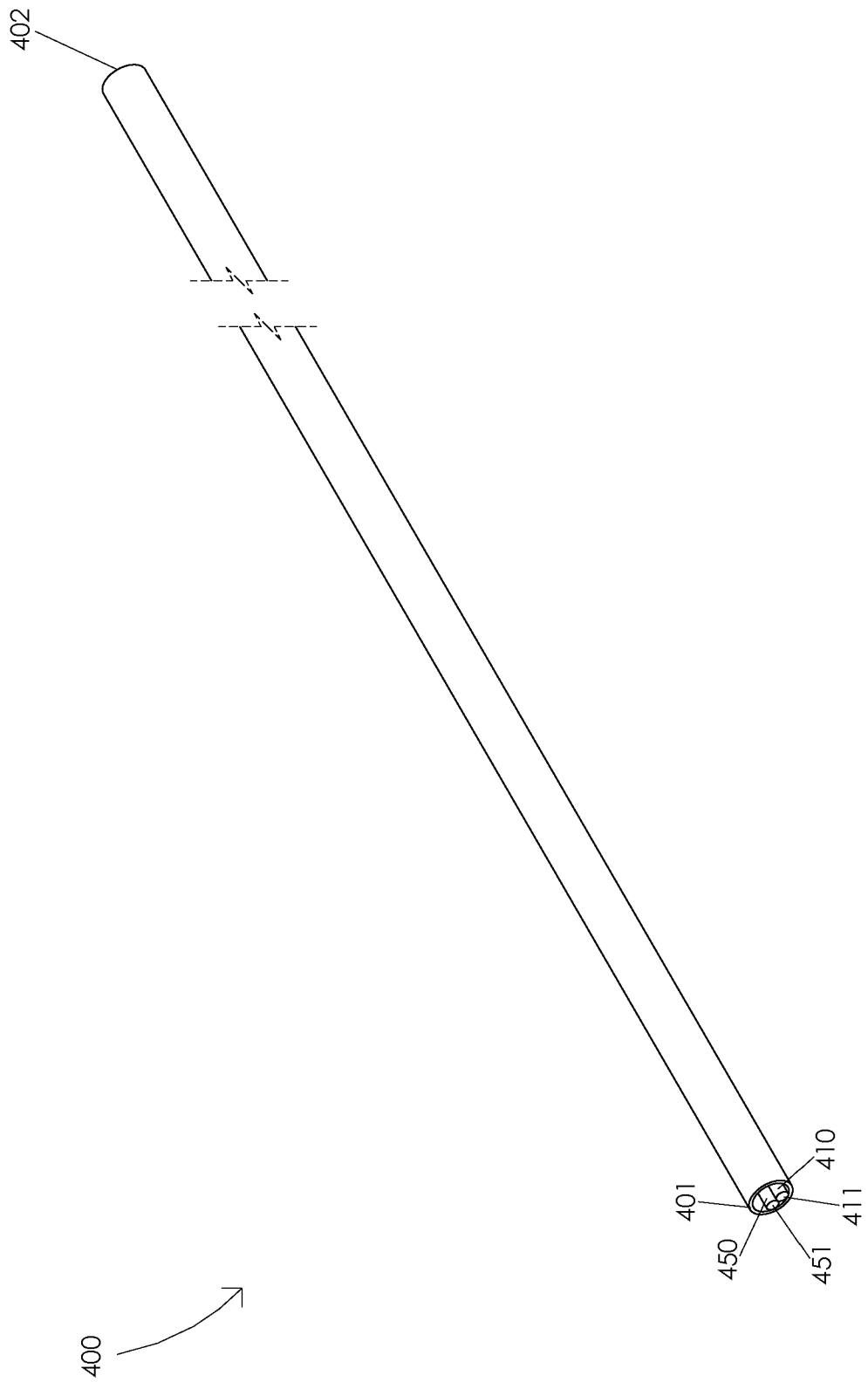
FIG. 4 is a schematic diagram illustrating a flexible housing tube.

FIG. 4 is a schematic diagram illustrating a flexible housing tube 400. Illustratively, flexible housing tube 400 may comprise a flexible housing tube distal end 401 and a flexible housing tube proximal end 402. Flexible housing tube 400 may be manufactured from any suitable material, e.g., polymers, metals, metal alloys, etc., or from any combination of suitable materials. Illustratively, flexible housing tube 400 may comprise a shape memory material, e.g., Nitinol. In one or more embodiments, flexible housing tube 400 may be manufactured from a material having an ultimate tensile strength between 700 and 1000 MPa. Illustratively, flexible housing tube 400 may be manufactured from a material having ultimate tensile strength less than 700 MPa or greater than 1000 MPa. In one or more embodiments, flexible housing tube 400 may be manufactured from a material having a modulus of elasticity between 30 and 80 GPa. Illustratively, flexible housing tube 400 may be manufactured from a material having a modulus of elasticity less than 30 GPa or greater than 80 GPa.

In one or more embodiments, flexible housing tube 400 may be manufactured with dimensions suitable for performing microsurgical procedures, e.g., ophthalmic surgical procedures. Illustratively, flexible housing tube 400 may be manufactured at gauge sizes commonly used in ophthalmic surgical procedures, e.g., 23 gauge, 25 gauge, etc. In one or more embodiments, flexible housing tube 400 may be configured to be inserted in a cannula, e.g., a cannula used during an ophthalmic surgical procedure. For example, one or more properties of flexible housing tube 400 may be optimized to reduce friction as flexible housing tube 400 is inserted into a cannula. In one or more embodiments, one or more properties of flexible housing tube 400 may be optimized to reduce friction as flexible housing tube 400 is removed from a cannula. Illustratively, flexible housing tube 400 may have an ultimate tensile strength between 1000 MPa and 1100 MPa. In one or more embodiments, flexible housing tube 400 may have an ultimate tensile strength less than 1000 MPa or greater than 1100 MPa.

In one or more embodiments, an optic fiber 450 may be disposed within flexible housing tube 400. Illustratively, optic fiber 450 may comprise an optic fiber distal end 451 and an optic fiber proximal end 452. In one or more embodiments, optic fiber 450 may be configured to transmit light, e.g., laser light. Illustratively, optic fiber 450 may be disposed within flexible housing tube 400 wherein optic fiber distal end 451 may be adjacent to flexible housing tube distal end 401. In one or more embodiments, a portion of optic fiber 450 may be fixed to a portion of flexible housing tube 400, e.g., by an adhesive or any suitable fixation means.

Illustratively, a cable 410 may be disposed within flexible housing tube 400. In one or more embodiments, cable 410 may comprise a cable distal end 411 and a cable proximal end 412. Illustratively, cable 410 may be disposed within flexible housing tube 400 wherein cable distal end 411 may be adjacent to flexible housing tube distal end 401. In one or more embodiments, cable 410 may be fixed to a portion of housing tube 400, e.g., by an adhesive or any suitable fixation means. For example, a portion of cable 410 may be fixed to a portion of flexible housing tube 400 by a weld, a press fit, a loop, a tie, etc.

Figure 5:
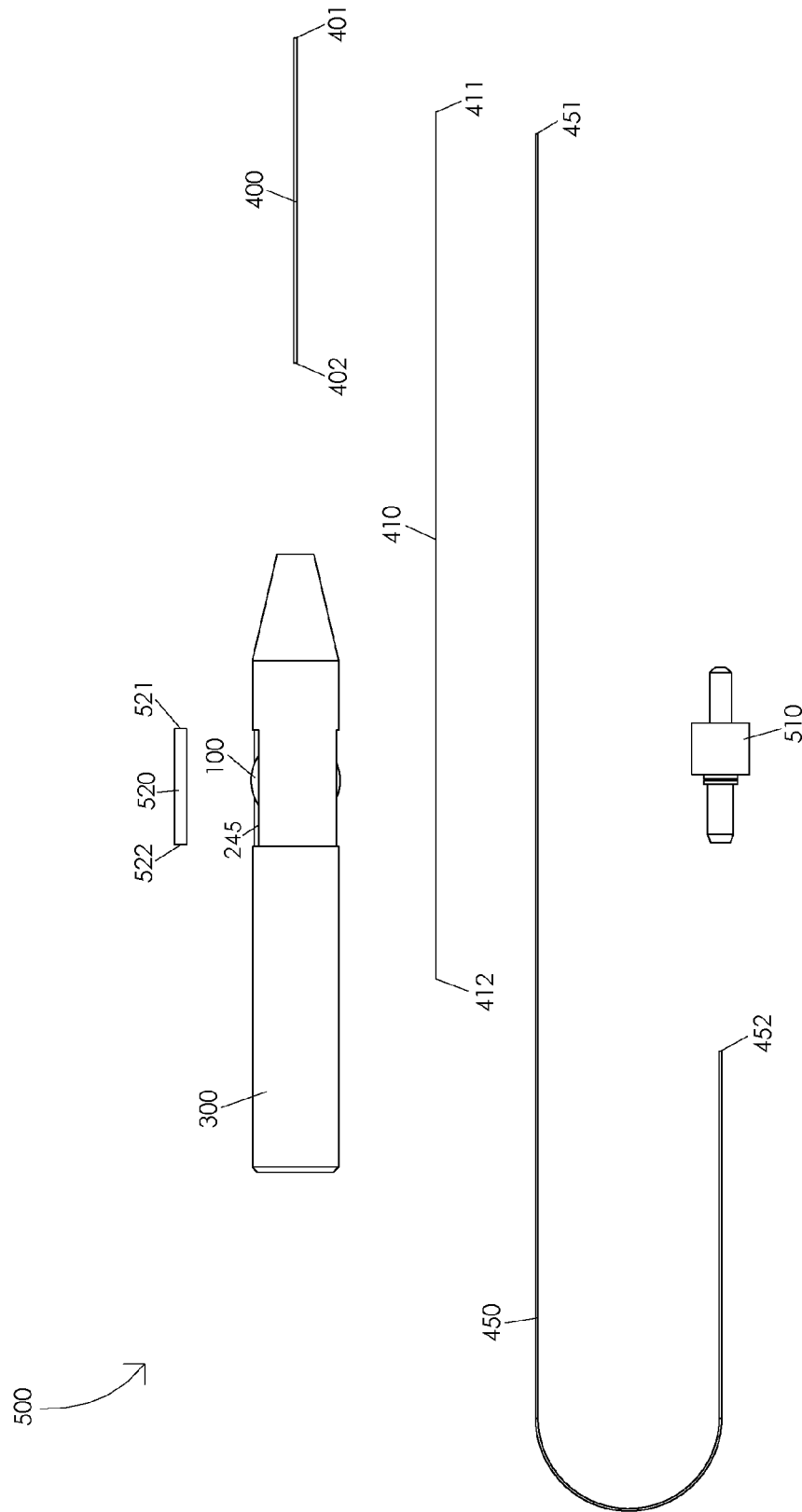
FIG. 5 is a schematic diagram illustrating an exploded view of a steerable laser probe assembly.

FIG. 5 is a schematic diagram illustrating an exploded view of a steerable laser probe assembly 500. In one or more embodiments, a steerable laser probe assembly 500 may comprise a handle 300 having a handle distal end 301 and a handle proximal end 302, a flexible housing tube 400 having a flexible housing tube distal end 401 and a flexible housing tube proximal end 402, a cable 410 having a cable distal end 411 and a cable proximal end 412, an optic fiber 450 having an optic fiber distal end 451 and an optic fiber proximal end 452, an auto-fixing component 520 having an auto-fixing component distal end 521 and an auto-fixing component proximal end 522, and a light source interface 510. Illustratively, light source interface 510 may be configured to interface with optic fiber 450, e.g., at optic fiber proximal end 452. In one or more embodiments, light source interface 510 may comprise a standard light source connector, e.g., an SMA connector.

Illustratively, a portion of flexible housing tube 400 may be disposed within a portion of handle 300, e.g., flexible housing tube proximal end 402 may be disposed within a portion of handle 300. In one or more embodiments, a portion of flexible housing tube 400 may be disposed within a portion of handle base 220, e.g., flexible housing tube proximal end 402 may be disposed in flexible housing tube housing 250. Illustratively, a portion of flexible housing tube 400 may be fixed within a portion of handle 300, e.g., flexible housing tube proximal end 402 may be fixed within flexible housing tube housing 250. In one or more embodiments, a portion of flexible housing tube 400 may be fixed within flexible housing tube housing 250, e.g., by an adhesive or any suitable fixation means. For example, a portion of flexible housing tube 400 may be fixed within flexible housing tube housing 250 by a press fit, a set screw, etc.

Illustratively, optic fiber 450 may be disposed within handle inner portion 240, actuation chamber 130, flexible housing tube housing 250, and flexible housing tube 400. In one or more embodiments, optic fiber 450 may be disposed within flexible housing tube 400 wherein optic fiber distal end 451 may be adjacent to flexible housing tube distal end 401. Illustratively, a portion of optic fiber 450 may be fixed to a portion of flexible housing tube 400, e.g., by an adhesive or any suitable fixation means. In one or more embodiments, cable 410 may be disposed within cable housing 120, actuation chamber 130, handle inner portion 240, flexible housing tube housing 250, and flexible housing tube 400. Illustratively, cable 410 may be disposed within flexible housing tube 400 wherein cable distal end 411 may be adjacent to flexible housing tube distal end 401. In one or more embodiments, a portion of cable 410 may be fixed to a portion of flexible housing tube 400, e.g., by an adhesive or any suitable fixation means. For example, a portion of cable 410 may be fixed to a portion of flexible housing tube 400 by a weld, a press fit, a loop, a tie, etc. In one or more embodiments, a portion of cable 410 may be fixed within cable housing 120, e.g., by an adhesive or any suitable fixation means. For example, a portion of cable 410 may be fixed within cable housing 120 by a weld, a press fit, a loop, a tie, etc. Illustratively, a first portion of cable 410 may be fixed to a portion of flexible housing tube 400 and a second portion of cable 410 may be fixed within cable housing 120. In one or more embodiments, cable distal end 411 may be fixed to a portion of flexible housing tube 400. Illustratively, cable proximal end 412 may be fixed within cable housing 120.

In one or more embodiments, a surgeon may rotate actuation control 100 within handle inner portion 240, e.g., by applying a force to a portion of actuation control 100. Illustratively, actuation chamber 130 may be configured to prevent a contact between a portion of actuation control 100 and a portion of optic fiber 450, e.g., due to a rotation of actuation control 100. In one or more embodiments, a geometry of actuation chamber 130 may be configured to prevent a contact between a portion of actuation control 100 and a portion of optic fiber 450, e.g., due to a rotation of actuation control. Illustratively, a surgeon may rotate actuation control 100 about fixation pin 215, e.g., by applying a force to a portion of actuation control 100. In one or more embodiments, a rotation of actuation control 100 may be configured to retract cable 410 relative to flexible housing tube 400. Illustratively, a retraction of cable 410 relative to flexible housing tube 400 may be configured to apply a force to a portion of flexible housing tube 400. In one or more embodiments, an application of a force to a portion of flexible housing tube 400 may be configured to compress a portion of flexible housing tube 400. Illustratively, a compression of a portion of flexible housing tube 400 may be configured to cause flexible housing tube 400 to gradually curve. In one or more embodiments, a gradual curving of flexible housing tube 400 may be configured to gradually curve optic fiber 450. Illustratively, a rotation of actuation control 100 may be configured to gradually curve optic fiber 450.

In one or more embodiments, a rotation of actuation control 100 may be configured to extend cable 410 relative to flexible housing tube 400. Illustratively, an extension of cable 410 relative to flexible housing tube 400 may be configured to reduce a force applied to a portion of flexible housing tube 400. In one or more embodiments, a reduction of a force applied to a portion of flexible housing tube 400 may be configured to decompress a portion of flexible housing tube 400. Illustratively, a decompression of a portion of flexible housing tube 400 may be configured to cause flexible housing tube 400 to gradually straighten. In one or more embodiments, a gradual straightening of flexible housing tube 400 may be configured to gradually straighten optic fiber 450. Illustratively, a rotation of actuation control 100 may be configured to gradually straighten optic fiber 450.

In one or more embodiments, auto-fixing component 520 may be disposed within auto-fixing component housing 245. Illustratively, auto-fixing component 520 may be fixed within auto-fixing component housing 245, e.g., by an adhesive or any suitable fixation means. In one or more embodiments, auto-fixing component 520 may be disposed within auto-fixing component housing 245 wherein a portion of auto-fixing component 520 may be adjacent to a portion of actuation control 100. Illustratively, auto-fixing component 520 may be configured to produce a magnetic field, e.g., auto-fixing component 520 may comprise a permanent magnet. In one or more embodiments, auto-fixing component 520 may comprise a ferromagnetic material, e.g., auto-fixing component 520 may comprise a ferrimagnetic material. Illustratively, actuation control 100 may be configured to produce a magnetic field, e.g., actuation control 100 may comprise a permanent magnetic. In one or more embodiments, actuation control 100 may comprise a ferromagnetic material, e.g., actuation control 100 may comprise a ferrimagnetic material.

Illustratively, auto-fixing component 520 may be configured to temporarily fix actuation control 100 in a rotational position within handle inner portion 240, e.g., a magnetic force attracting actuation control 100 to auto-fixing component 520 may be configured to hold actuation control 100 fixed in a rotational position within handle inner portion 240. In one or more embodiments, actuation control 100 may be configured to temporarily fix actuation control 100 in a rotational position within handle inner portion 240, e.g., a magnetic force attracting auto-fixing component 520 to actuation control 100 may be configured to temporarily hold actuation control 100 fixed in a rotational position within handle inner portion 240. Illustratively, both auto-fixing component 520 and actuation control 100 may be configured to temporarily fix actuation control 100 in a rotational position within handle inner portion 240, e.g., auto-fixing component 520 and actuation control 100 may both comprise permanent magnets having poles oriented to attract auto-fixing component 520 to actuation control 100 and to attract actuation control 100 to auto-fixing component 520.

In one or more embodiments, a surgeon may actuate actuation control 100 within handle inner portion 240, e.g., by applying a force to a portion of actuation control 100 until actuation control 100 is in a first desired rotational position within handle inner portion 240. Illustratively, the surgeon may then remove the force applied to actuation control 100 and perform a portion of a surgical procedure, e.g., actuation control 100 and auto-fixing component 520 may be configured to temporarily fix actuation control 100 in the first desired rotational position within handle inner portion 240. In one or more embodiments, the surgeon may actuate actuation control 100 within handle inner portion 240, e.g., by applying a force to a portion of actuation control 100 until actuation control 100 is in a second desired rotational position within handle inner portion 240. Illustratively, the surgeon may then remove the force applied to actuation control 100 and perform a portion of a surgical procedure, e.g., actuation control 100 and auto-fixing component 520 may be configured to temporarily fix actuation control 100 in the second desired rotational position within handle inner portion 240. In one or more embodiments, the surgeon may actuate actuation control 100 within handle inner portion 240, e.g., by applying a force to a portion of actuation control 100 until actuation control 100 is in a third desired rotational position within handle inner portion 240. Illustratively, the surgeon may then remove the force applied to actuation control 100 and perform a portion of a surgical procedure, e.g., actuation control 100 and auto-fixing component 520 may be configured to temporarily fix actuation control 100 in the third desired rotational position within handle inner portion 240. In one or more embodiments, actuation control 100 and auto-fixing component 520 may be configured to temporarily fix actuation control 100 in any desired rotational position within handle inner portion 240.

Figure 6A:
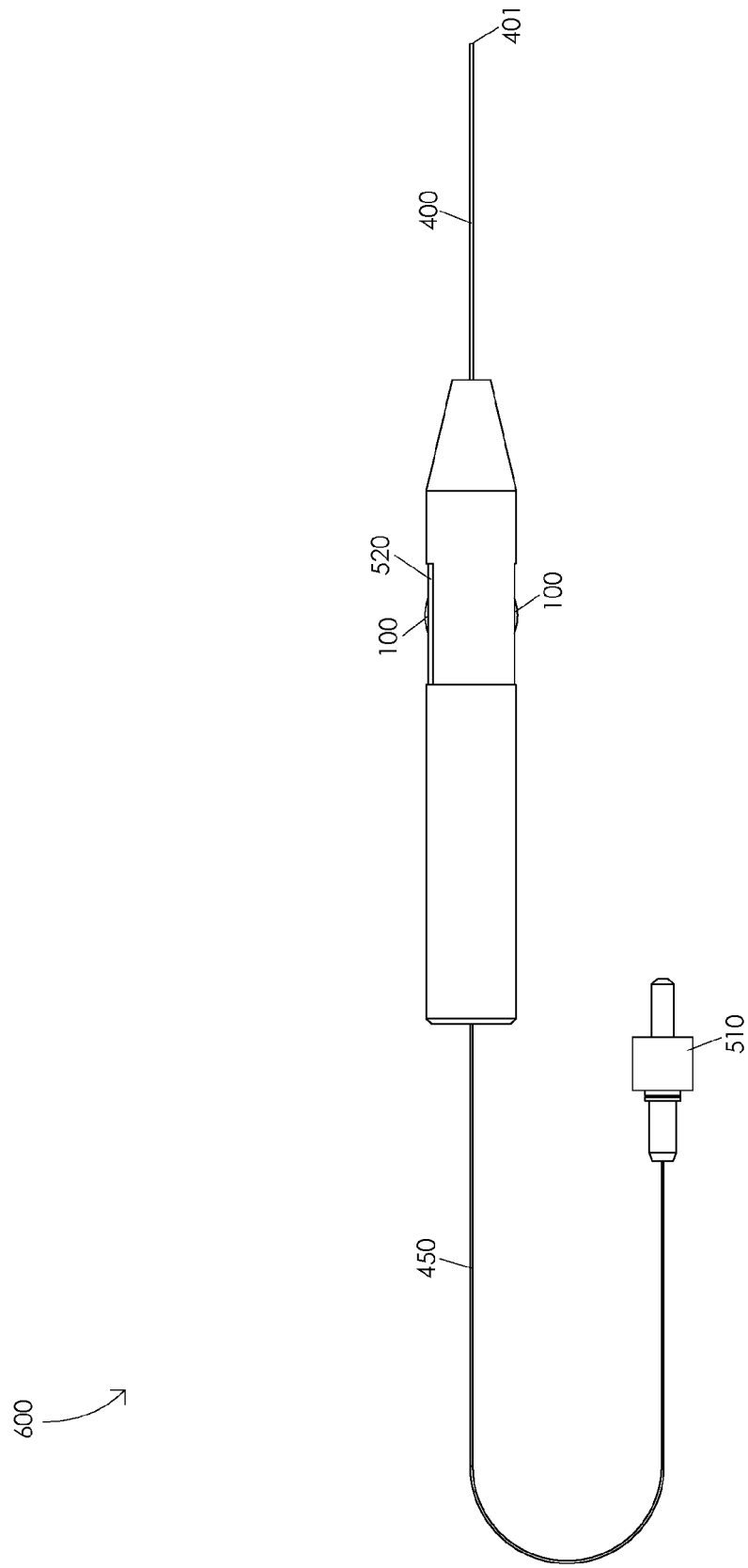
FIGS. 6A, 6B, 6C, 6D, and 6E are schematic diagrams illustrating a gradual curving of an optic fiber.

FIGS. 6A, 6B, 6C, 6D, and 6E are schematic diagrams illustrating a gradual curving of an optic fiber 450. FIG. 6A illustrates a straight optic fiber 600. In one or more embodiments, optic fiber 450 may comprise a straight optic fiber 600, e.g., when cable 410 is fully extended relative to flexible housing tube 400. Illustratively, a line tangent to optic fiber distal end 451 may be parallel to a line tangent to flexible housing tube proximal end 402, e.g., when optic fiber 450 comprises a straight optic fiber 600. In one or more embodiments, actuation control 100 and auto-fixing component 520 may be configured to temporarily fix actuation control 100 in a first fixed rotational position within handle inner portion 240. Illustratively, optic fiber 450 may comprise a straight optic fiber 600, e.g., when actuation control 100 is fixed in the first fixed rotational position within handle inner portion 240.

Figure 6B:
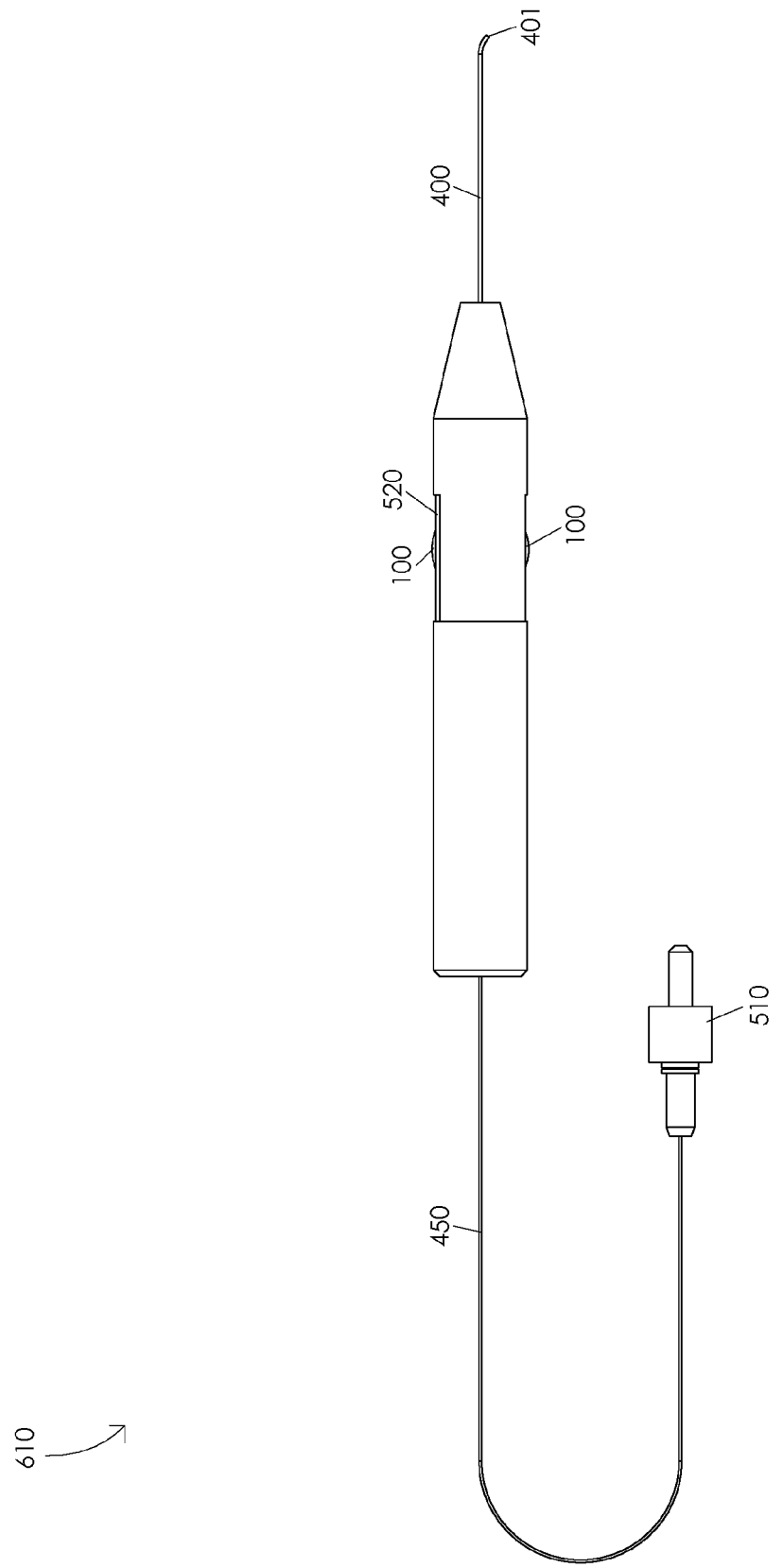

FIG. 6B illustrates an optic fiber in a first curved position 610. In one or more embodiments, a rotation of actuation control 100 within handle inner portion 240 may be configured to gradually curve optic fiber 450 from a straight optic fiber 600 to an optic fiber in a first curved position 610. Illustratively, a rotation of actuation control 100 within handle inner portion 240 may be configured to retract cable 410 relative to flexible housing tube 400. In one or more embodiments, a retraction of cable 410 relative to flexible housing tube 400 may be configured to apply a force to a portion of flexible housing tube 400. Illustratively, an application of a force to a portion of flexible housing tube 400 may be configured to compress a portion of flexible housing tube 400. In one or more embodiments, a compression of a portion of flexible housing tube 400 may be configured to gradually curve flexible housing tube 400. Illustratively, a gradual curving of flexible housing tube 400 may be configured to gradually curve optic fiber 450, e.g., from a straight optic fiber 600 to an optic fiber in a first curved position 610. In one or more embodiments, a line tangent to optic fiber distal end 451 may intersect a line tangent to flexible housing tube proximal end 402 at a first angle, e.g., when optic fiber 450 comprises an optic fiber in a first curved position 610. In one or more embodiments, the first angle may comprise any angle greater than zero degrees. For example, the first angle may comprise a 45 degree angle. Illustratively, actuation control 100 and auto-fixing component 520 may be configured to temporarily fix actuation control 100 in a second fixed rotational position within handle inner portion 240. In one or more embodiments, optic fiber 450 may comprise an optic fiber in a first curved position 610, e.g., when actuation control 100 is fixed in the second fixed rotational position within handle inner portion 240.

Figure 6C:
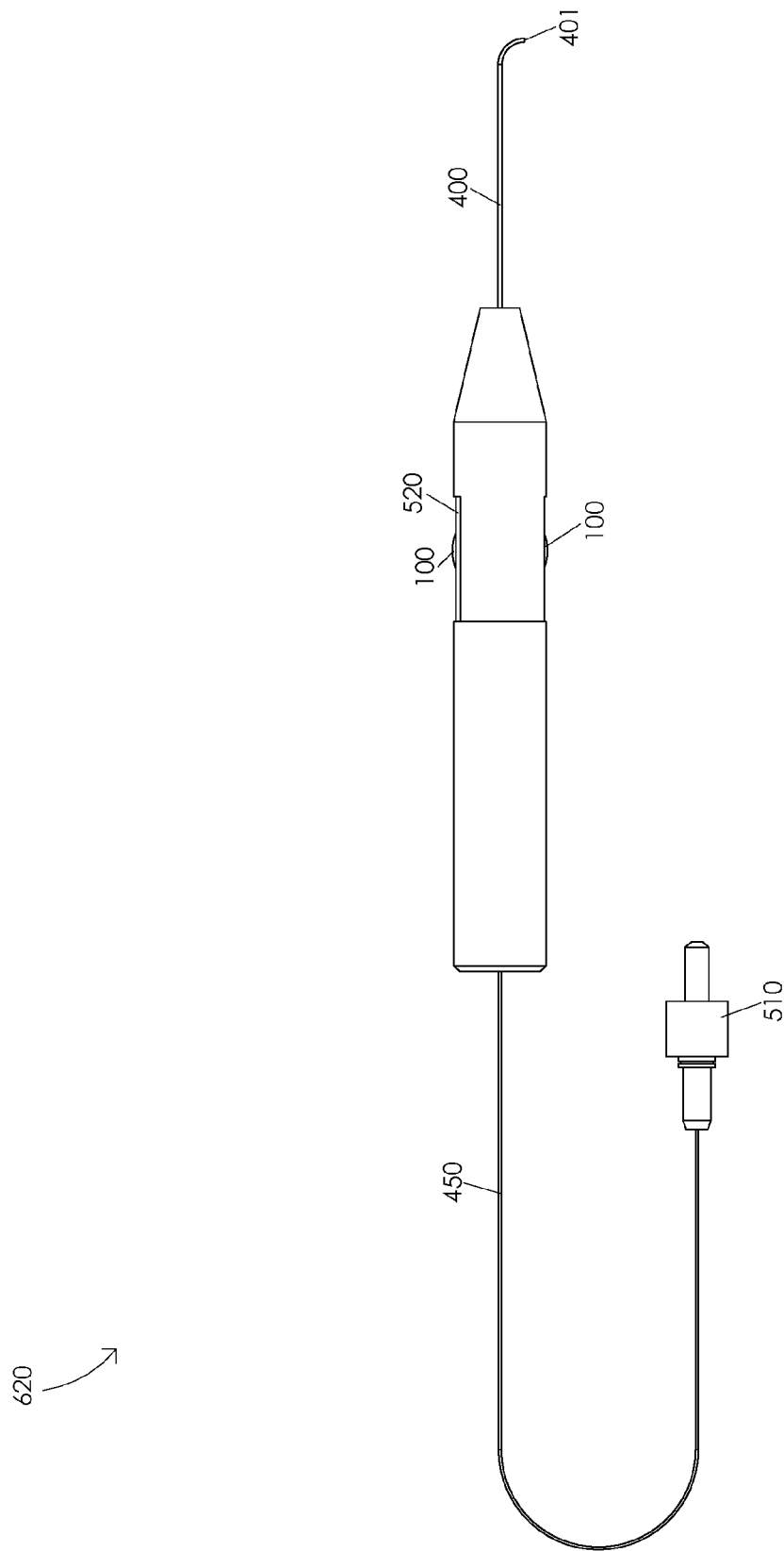

FIG. 6C illustrates an optic fiber in a second curved position 620. In one or more embodiments, a rotation of actuation control 100 within handle inner portion 240 may be configured to gradually curve optic fiber 450 from an optic fiber in a first curved position 610 to an optic fiber in a second curved position 620. Illustratively, a rotation of actuation control 100 within handle inner portion 240 may be configured to retract cable 410 relative to flexible housing tube 400. In one or more embodiments, a retraction of cable 410 relative to flexible housing tube 400 may be configured to apply a force to a portion of flexible housing tube 400. Illustratively, an application of a force to a portion of flexible housing tube 400 may be configured to compress a portion of flexible housing tube 400. In one or more embodiments, a compression of a portion of flexible housing tube 400 may be configured to gradually curve flexible housing tube 400. Illustratively, a gradual curving of flexible housing tube 400 may be configured to gradually curve optic fiber 450, e.g., from an optic fiber in a first curved position 610 to an optic fiber in a second curved position 620. In one or more embodiments, a line tangent to optic fiber distal end 451 may intersect a line tangent to flexible housing tube proximal end 402 at a second angle, e.g., when optic fiber 450 comprises an optic fiber in a second curved position 620. In one or more embodiments, the second angle may comprise any angle greater than the first angle. For example, the second angle may comprise a 90 degree angle. Illustratively, actuation control 100 and auto-fixing component 520 may be configured to temporarily fix actuation control 100 in a third fixed rotational position within handle inner portion 240. In one or more embodiments, optic fiber 450 may comprise an optic fiber in a second curved position 620, e.g., when actuation control 100 is fixed in the third fixed rotational position within handle inner portion 240.

Figure 6D:
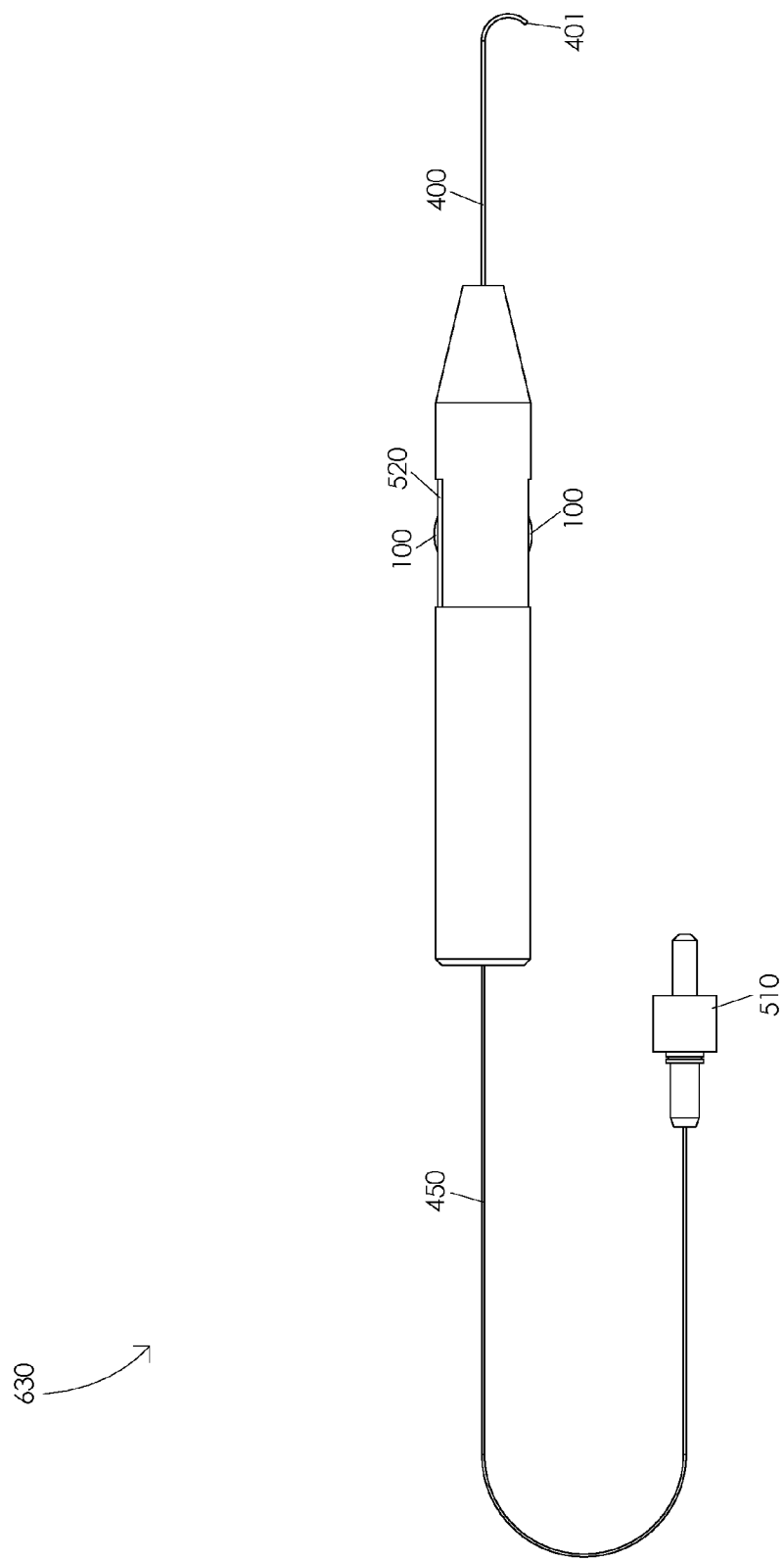

FIG. 6D illustrates an optic fiber in a third curved position 630. In one or more embodiments, a rotation of actuation control 100 within handle inner portion 240 may be configured to gradually curve optic fiber 450 from an optic fiber in a second curved position 620 to an optic fiber in a third curved position 630. Illustratively, a rotation of actuation control 100 within handle inner portion 240 may be configured to retract cable 410 relative to flexible housing tube 400. In one or more embodiments, a retraction of cable 410 relative to flexible housing tube 400 may be configured to apply a force to a portion of flexible housing tube 400. Illustratively, an application of a force to a portion of flexible housing tube 400 may be configured to compress a portion of flexible housing tube 400. In one or more embodiments, a compression of a portion of flexible housing tube 400 may be configured to gradually curve flexible housing tube 400. Illustratively, a gradual curving of flexible housing tube 400 may be configured to gradually curve optic fiber 450, e.g., from an optic fiber in a second curved position 620 to an optic fiber in a third curved position 630. In one or more embodiments, a line tangent to optic fiber distal end 451 may intersect a line tangent to flexible housing tube proximal end 402 at a third angle, e.g., when optic fiber 450 comprises an optic fiber in a third curved position 630. In one or more embodiments, the third angle may comprise any angle greater than the second angle. For example, the third angle may comprise a 135 degree angle. Illustratively, actuation control 100 and auto-fixing component 520 may be configured to temporarily fix actuation control 100 in a fourth fixed rotational position within handle inner portion 240. In one or more embodiments, optic fiber 450 may comprise an optic fiber in a third curved position 630, e.g., when actuation control 100 is fixed in the fourth fixed rotational position within handle inner portion 240.

Figure 6E:
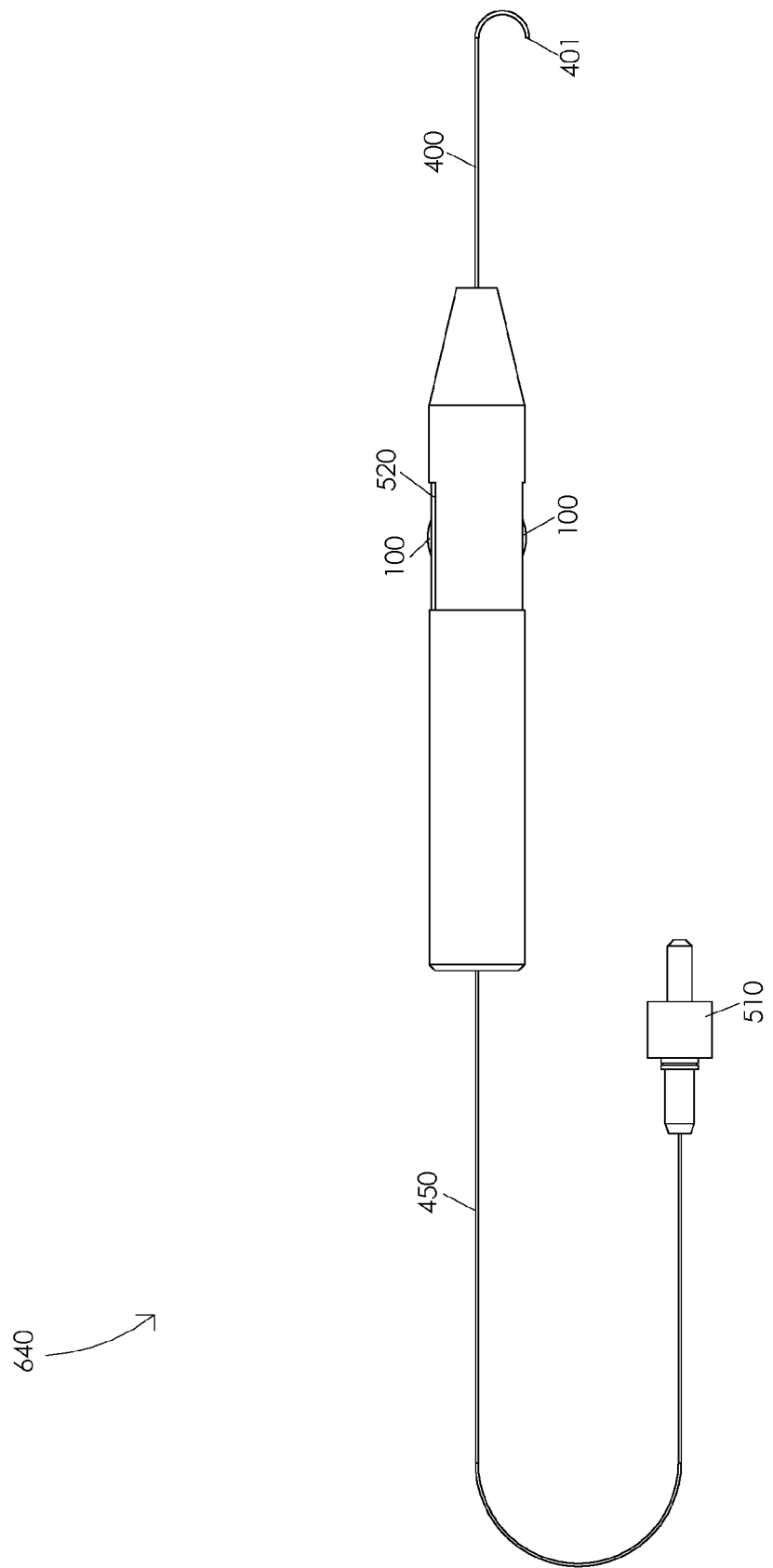

FIG. 6E illustrates an optic fiber in a fourth curved position 640. In one or more embodiments, a rotation of actuation control 100 within handle inner portion 240 may be configured to gradually curve optic fiber 450 from an optic fiber in a third curved position 630 to an optic fiber in a fourth curved position 640. Illustratively, a rotation of actuation control 100 within handle inner portion 240 may be configured to retract cable 410 relative to flexible housing tube 400. In one or more embodiments, a retraction of cable 410 relative to flexible housing tube 400 may be configured to apply a force to a portion of flexible housing tube 400. Illustratively, an application of a force to a portion of flexible housing tube 400 may be configured to compress a portion of flexible housing tube 400. In one or more embodiments, a compression of a portion of flexible housing tube 400 may be configured to gradually curve flexible housing tube 400. Illustratively, a gradual curving of flexible housing tube 400 may be configured to gradually curve optic fiber 450, e.g., from an optic fiber in a third curved position 630 to an optic fiber in a fourth curved position 640. In one or more embodiments, a line tangent to optic fiber distal end 451 may be parallel to a line tangent to flexible housing tube proximal end 402, e.g., when optic fiber 450 comprises an optic fiber in a fourth curved position 640. Illustratively, actuation control 100 and auto-fixing component 520 may be configured to temporarily fix actuation control 100 in a fifth fixed rotational position within handle inner portion 240. In one or more embodiments, optic fiber 450 may comprise an optic fiber in a fourth curved position 640, e.g., when actuation control 100 is fixed in the fifth fixed rotational position within handle inner portion 240.

In one or more embodiments, one or more properties of a steerable laser probe may be adjusted to attain one or more desired steerable laser probe features. Illustratively, a distance that flexible housing tube distal end 401 extends from handle distal end 301 may be adjusted to vary an amount of rotation of actuation control 100 configured to curve flexible housing tube 400 to a particular curved position. In one or more embodiments, a stiffness of flexible housing tube 400 may be adjusted to vary an amount of rotation of actuation control 100 configured to curve flexible housing tube 400 to a particular curved position. Illustratively, a material comprising flexible housing tube 400 may be adjusted to vary an amount of rotation of actuation control 100 configured to curve flexible housing tube 400 to a particular curved position. In one or more embodiments, a stiffness of flexible housing tube 400 may be adjusted to vary a bend radius of flexible housing tube 400. Illustratively, a stiffness of flexible housing tube 400 may be adjusted to vary a radius of curvature of flexible housing tube 400, e.g., when flexible housing tube 400 is in a particular curved position.

In one or more embodiments, at least a portion of optic fiber 450 may be enclosed in an optic fiber sleeve configured to, e.g., protect optic fiber 450, vary a stiffness of optic fiber 450, vary an optical property of optic fiber 450, etc. Illustratively, optic fiber 450 may comprise a buffer, a cladding disposed in the buffer, and a core disposed in the cladding. In one or more embodiments, at least a portion of optic fiber 450 may comprise a buffer configured to protect an optical property of optic fiber 450. Illustratively, at least a portion of optic fiber 450 may comprise a buffer configured to protect an optical layer of optic fiber 450, e.g., the buffer may protect an optical layer of a curved portion of optic fiber 450. In one or more embodiments, at least a portion of optic fiber 450 may comprise a polyimide buffer configured to protect an optical property of optic fiber 450. For example, at least a portion of optic fiber 450 may comprise a Kapton buffer configured to protect an optical property of optic fiber 450.

In one or more embodiments, a location wherein cable 410 may be fixed to flexible housing tube 400 may be adjusted to vary an amount of rotation of actuation control 100 configured to curve flexible housing tube 400 to a particular curved position. For example, a portion of cable 410 may be fixed to an outer portion of flexible housing tube 400. Illustratively, cable 410 may be fixed to flexible housing tube 400 at a plurality of fixation points, e.g., to vary one or more properties of a steerable laser probe. In one or more embodiments, a length of cable 410 may be adjusted to vary an amount of rotation of actuation control 100 configured to curve flexible housing tube 400 to a particular curved position. Illustratively, a steerable laser probe may comprise one or more redundant cables 410. In one or more embodiments, one or more redundant cables 410 may be configured to maintain a particular curved position of flexible housing tube 400, e.g., in the event that cable 410 breaks or fails. Illustratively, one or more redundant cables 410 may be configured to maintain a particular curved position of flexible housing tube 400, e.g., in the event that a cable 410 fixation means fails. In one or more embodiments, one or more redundant cables 410 may be configured to maintain a particular curved position of flexible housing tube 400, e.g., in the event that cable 410 is no longer configured to maintain the particular curved position of flexible housing tube 400. Illustratively, one or more redundant cables 410 may be configured to maintain a particular curved position of flexible housing tube 400 wherein cable 410 is also configured to maintain the particular curved position of flexible housing tube 400.

In one or more embodiments, flexible housing tube 400 may comprise an access window configured to allow access to a portion cable 410. Illustratively, cable 410 may be fixed to a portion of flexible housing tube 400, e.g., by looping a portion of cable 410 through an aperture in flexible housing tube 400. In one or more embodiments, cable 410 may be fixed to a portion of flexible housing tube 400, e.g., by a purely mechanical means. For example, cable 410 may be fixed to a portion of flexible housing tube 400 in a manner other than by an adhesive, a weld, etc. Illustratively, cable 410 may be fixed to a portion of flexible housing tube 400 wherein a portion of cable 410 is configured to fail at a first applied failure force and a fixation means that fixes a portion of cable 410 to a portion of flexible housing tube 400 is configured to fail at a second applied failure force. In one or more embodiments, the second applied failure force may be greater than the first applied failure force.

Illustratively, an arrangement of a portion of cable 410, e.g., an arrangement of a portion of cable 410 between cable distal end 411 and cable proximal end 412, may be adjusted to attain one or more desired steerable laser probe features. In one or more embodiments, an arrangement of a portion of cable 410 may be configured to cause a rotation of actuation control 100, e.g., a rotation of actuation control 100 due to force vector applied to actuation control anterior end 103 and directed towards handle distal end 301 and away from handle proximal end 302, to retract cable 410 relative to flexible housing tube 400. Illustratively, an arrangement of a portion of cable 410 may be configured to cause a rotation of actuation control 100, e.g., a rotation of actuation control 100 due to force vector applied to actuation control anterior end 103 and directed towards handle proximal end 302 and away from handle distal end 301, to extend cable 410 relative to flexible housing tube 400. In one or more embodiments, cable 410 may be disposed within actuation chamber 130, e.g., cable 410 may ingress actuation chamber 130 at actuation control distal end 101, and then disposed within cable housing 120. Illustratively, cable 410 may be disposed within actuation chamber 130, e.g., cable 410 may be disposed over actuation control posterior end 104 and ingress actuation chamber 130 at actuation control proximal end 102, and then disposed within cable housing 120. In one or more embodiments, cable 410 may not be disposed within actuation chamber 130, e.g., cable 410 may be disposed over actuation control posterior end 104 and actuation control proximal end 102, and then disposed within cable housing 120.

Illustratively, an arrangement of a portion of cable 410 may be configured to cause a rotation of actuation control 100, e.g., a rotation of actuation control 100 due to force vector applied to actuation control anterior end 103 and directed towards handle proximal end 302 and away from handle distal end 301, to retract cable 410 relative to flexible housing tube 400. In one or more embodiments, an arrangement of a portion of cable 410 may be configured to cause a rotation of actuation control 100, e.g., a rotation of actuation control 100 due to force vector applied to actuation control anterior end 103 and directed towards handle distal end 301 and away from handle proximal end 302, to extend cable 410 relative to flexible housing tube 400. For example, cable 410 may be disposed over a portion of actuation control 100 between actuation control distal end 101 and actuation control anterior end 103, and then disposed within cable housing 120.

Illustratively, a steerable laser probe may be configured to indicate, e.g., to a surgeon, a direction that optic fiber 450 may curve, e.g., due to a rotation of actuation control 100 within handle inner portion 240. In one or more embodiments, a portion of a steerable laser probe, e.g., handle 300, may be marked in a manner configured to indicate a direction that optic fiber 450 may curve. For example, a portion of flexible housing tube 400 may comprise a mark configured to indicate a direction that optic fiber 450 may curve. Illustratively, flexible housing tube 400 may comprise a slight curve, e.g., a curve less than 7.5 degrees, when cable 410 is fully extended relative to flexible housing tube 400. For example, flexible housing tube 400 may comprise a slight curve, e.g., a curve greater than 7.5 degrees, when cable 410 is fully extended relative to flexible housing tube 400. In one or more embodiments, flexible housing tube 400 may comprise a slight curve configured to indicate a direction that optic fiber 450 may curve, e.g., due to a rotation of actuation control 100 within handle inner portion 240.

Figure 7A:
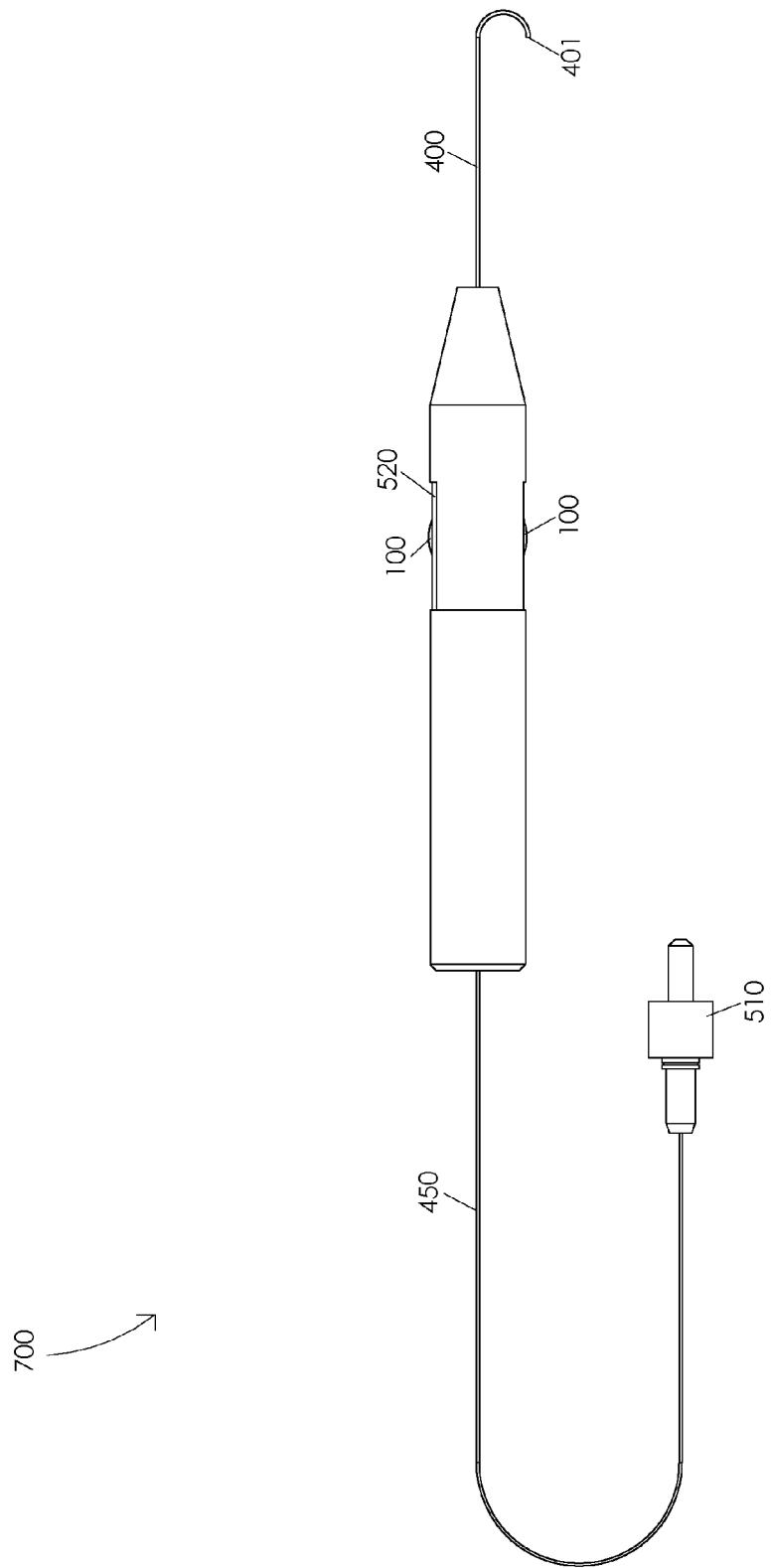
FIGS. 7A, 7B, 7C, 7D, and 7E are schematic diagrams illustrating a gradual straightening of an optic fiber.

FIGS. 7A, 7B, 7C, 7D, and 7E are schematic diagrams illustrating a gradual straightening of an optic fiber 450. FIG. 7A illustrates a fully curved optic fiber 700. In one or more embodiments, optic fiber 450 may comprise a fully curved optic fiber 700, e.g., when cable 410 is fully retracted relative to flexible housing tube 400. In one or more embodiments, a line tangent to optic fiber distal end 451 may be parallel to a line tangent to flexible housing tube proximal end 402, e.g., when optic fiber 450 comprises a fully curved optic fiber 700.

Figure 7B:
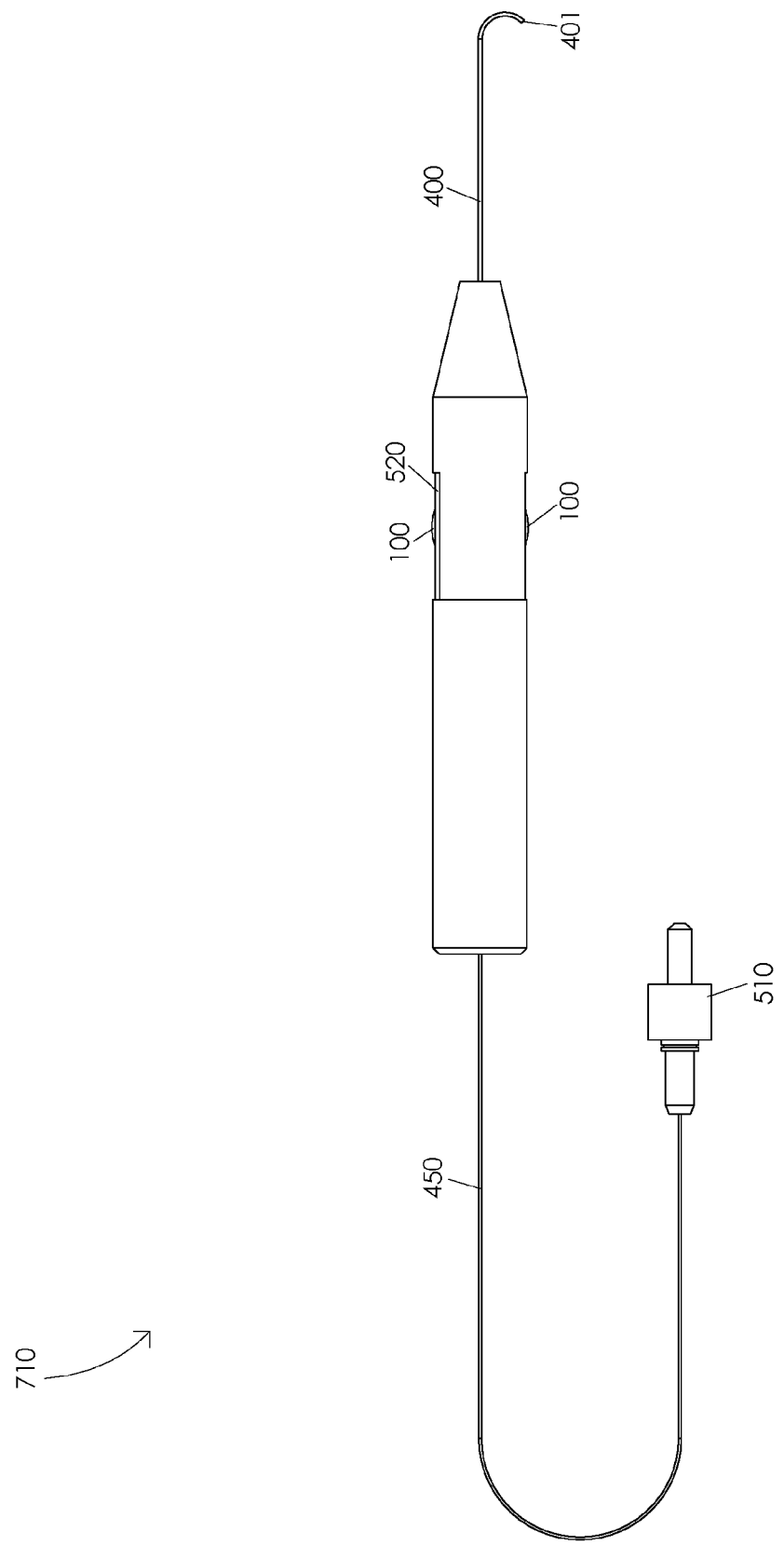

FIG. 7B illustrates an optic fiber in a first partially straightened position 710. In one or more embodiments, a rotation of actuation control 100 within handle inner portion 240 may be configured to gradually straighten optic fiber 450 from a fully curved optic fiber 700 to an optic fiber in a first partially straightened position 710. Illustratively, a rotation of actuation control 100 within handle inner portion 240 may be configured to extend cable 410 relative to flexible housing tube 400. In one or more embodiments, an extension of cable 410 relative to flexible housing tube 400 may be configured to reduce a force applied to flexible housing tube 400. Illustratively, a reduction of a force applied to a portion of flexible housing tube 400 may be configured to decompress a portion of flexible housing tube 400. In one or more embodiments, a decompression of a portion of flexible housing tube 400 may be configured to gradually straighten flexible housing tube 400. Illustratively, a gradual straightening of flexible housing tube 400 may be configured to gradually straighten optic fiber 450, e.g., from a fully curved optic fiber 700 to an optic fiber in a first partially straightened position 710. In one or more embodiments, a line tangent to optic fiber distal end 451 may intersect a line tangent to flexible housing tube proximal end 402 at a first partially straightened angle, e.g., when optic fiber 450 comprises an optic fiber in a first partially straightened position 710. Illustratively, the first partially straightened angle may comprise any angle less than 180 degrees. For example, the first partially straightened angle may comprise a 135 degree angle.

Figure 7C:
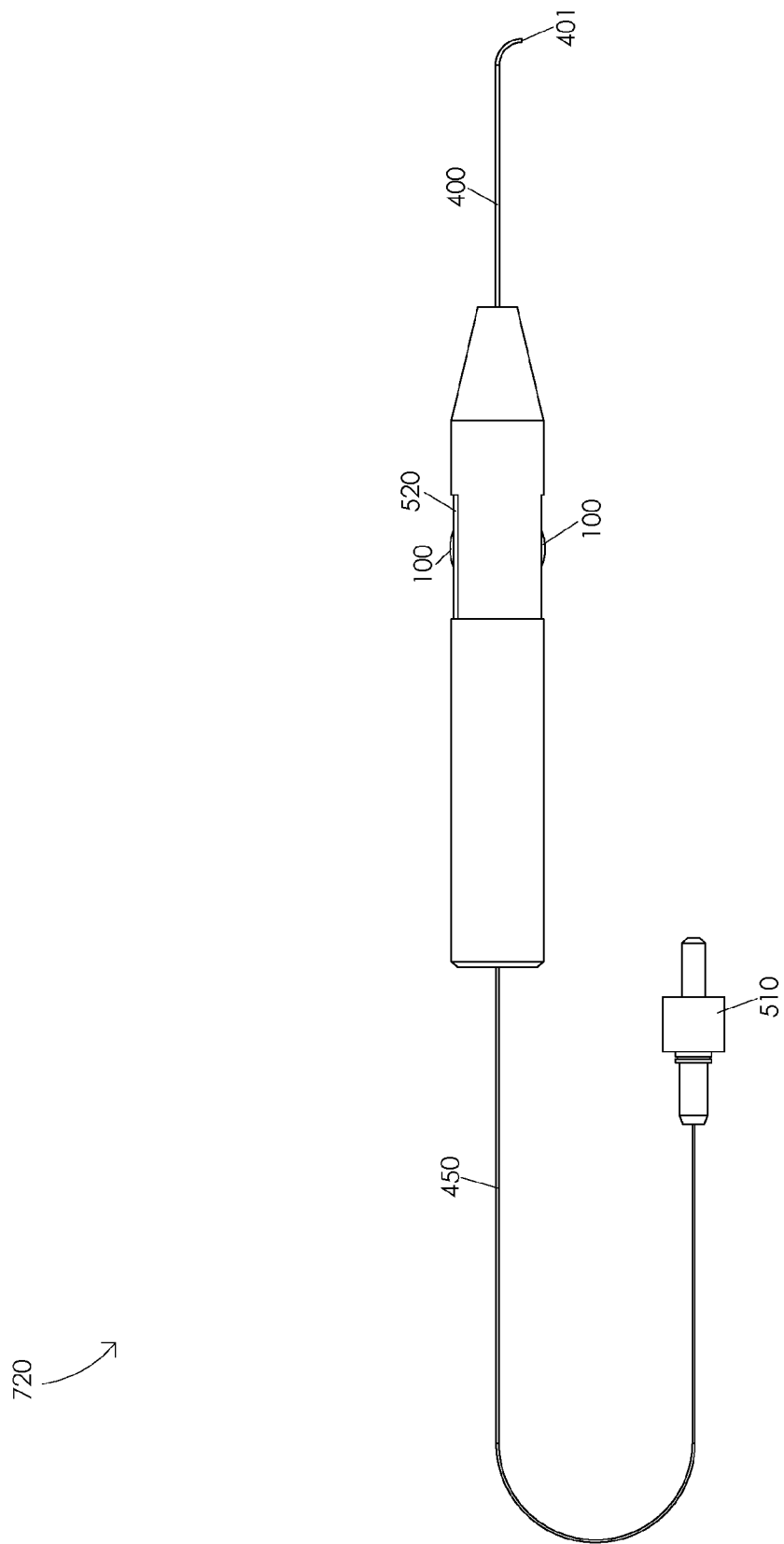

FIG. 7C illustrates an optic fiber in a second partially straightened position 720. In one or more embodiments, a rotation of actuation control 100 within handle inner portion 240 may be configured to gradually straighten optic fiber 450 from an optic fiber in a first partially straightened position 710 to an optic fiber in a second partially straightened position 720. Illustratively, a rotation of actuation control 100 within handle inner portion 240 may be configured to extend cable 410 relative to flexible housing tube 400. In one or more embodiments, an extension of cable 410 relative to flexible housing tube 400 may be configured to reduce a force applied to flexible housing tube 400. Illustratively, a reduction of a force applied to a portion of flexible housing tube 400 may be configured to decompress a portion of flexible housing tube 400. In one or more embodiments, a decompression of a portion of flexible housing tube 400 may be configured to gradually straighten flexible housing tube 400. Illustratively, a gradual straightening of flexible housing tube 400 may be configured to gradually straighten optic fiber 450, e.g., from an optic fiber in a first partially straightened position 710 to an optic fiber in a second partially straightened position 720. In one or more embodiments, a line tangent to optic fiber distal end 451 may intersect a line tangent to flexible housing tube proximal end 402 at a second partially straightened angle, e.g., when optic fiber 450 comprises an optic fiber in a second partially straightened position 720. Illustratively, the second partially straightened angle may comprise any angle less than the first partially straightened angle. For example, the second partially straightened angle may comprise a 90 degree angle.

Figure 7D:
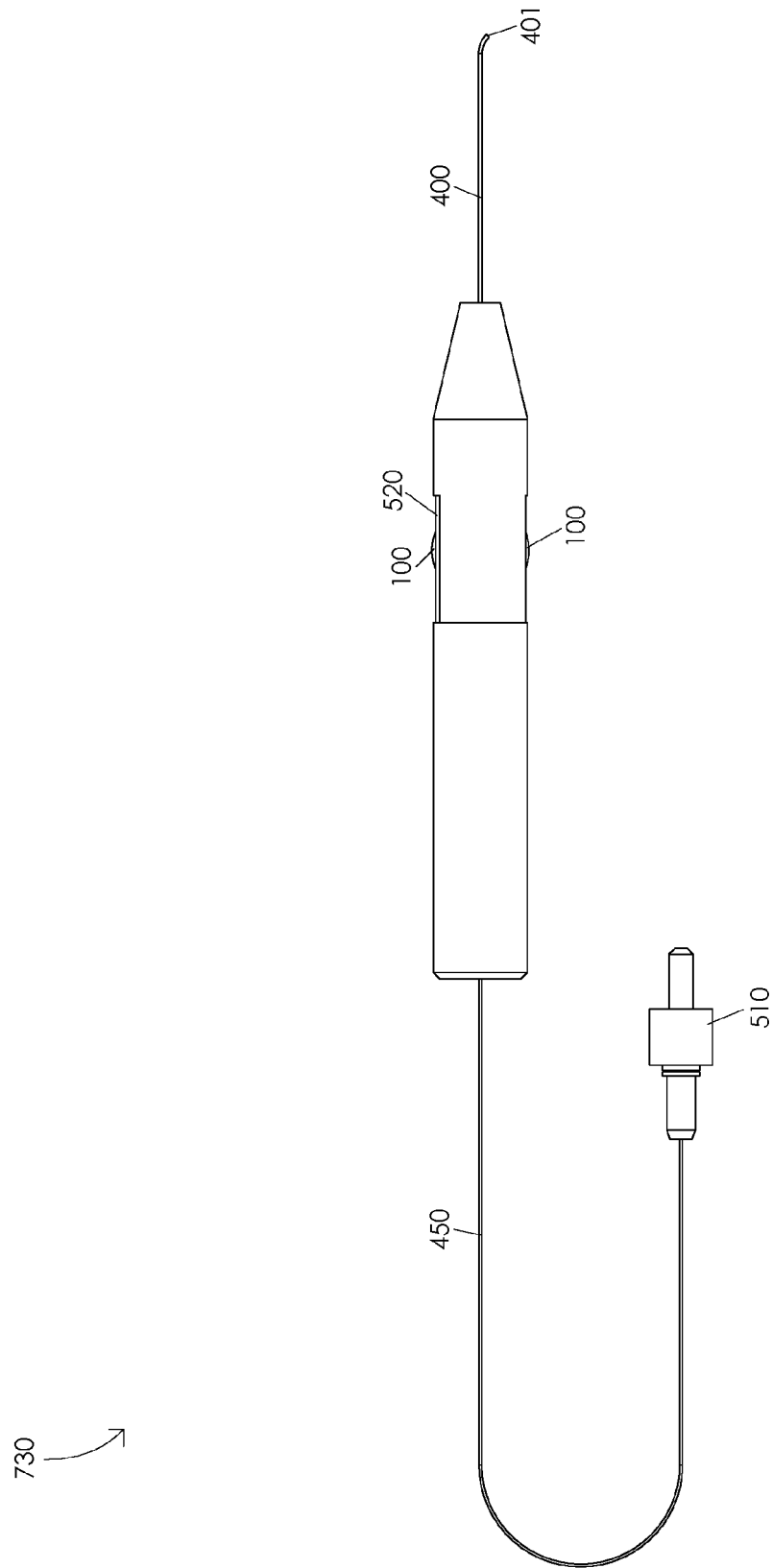

FIG. 7D illustrates an optic fiber in a third partially straightened position 730. In one or more embodiments, a rotation of actuation control 100 within handle inner portion 240 may be configured to gradually straighten optic fiber 450 from an optic fiber in a second partially straightened position 720 to an optic fiber in a third partially straightened position 730. Illustratively, a rotation of actuation control 100 within handle inner portion 240 may be configured to extend cable 410 relative to flexible housing tube 400. In one or more embodiments, an extension of cable 410 relative to flexible housing tube 400 may be configured to reduce a force applied to flexible housing tube 400. Illustratively, a reduction of a force applied to a portion of flexible housing tube 400 may be configured to decompress a portion of flexible housing tube 400. In one or more embodiments, a decompression of a portion of flexible housing tube 400 may be configured to gradually straighten flexible housing tube 400. Illustratively, a gradual straightening of flexible housing tube 400 may be configured to gradually straighten optic fiber 450, e.g., from an optic fiber in a second partially straightened position 720 to an optic fiber in a third partially straightened position 730. In one or more embodiments, a line tangent to optic fiber distal end 451 may intersect a line tangent to flexible housing tube proximal end 402 at a third partially straightened angle, e.g., when optic fiber 450 comprises an optic fiber in a third partially straightened position 730. Illustratively, the third partially straightened angle may comprise any angle less than the second partially straightened angle. For example, the third partially straightened angle may comprise a 45 degree angle.

Figure 7E:
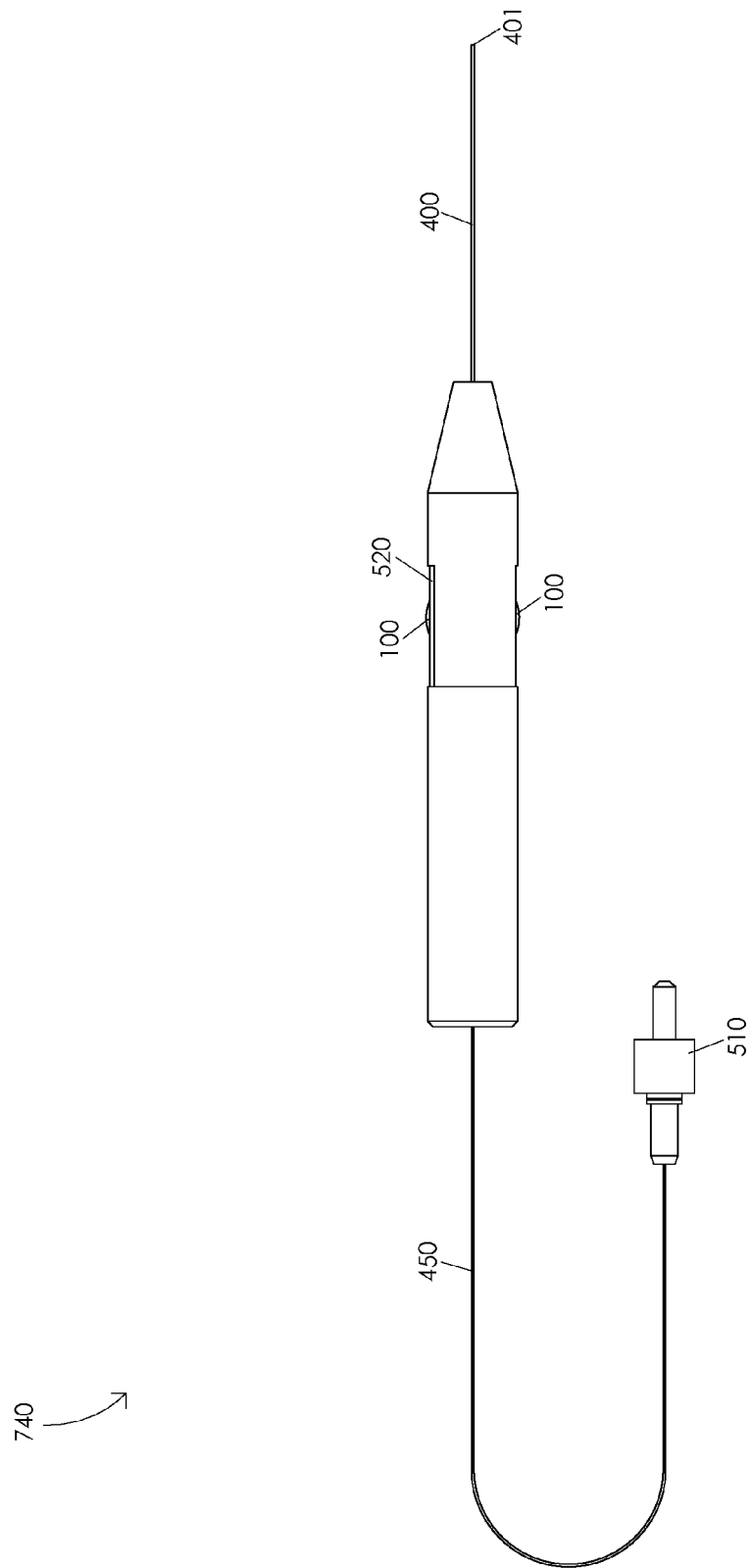

FIG. 7E illustrates an optic fiber in a fully straightened position 740. In one or more embodiments, a rotation of actuation control 100 within handle inner portion 240 may be configured to gradually straighten optic fiber 450 from an optic fiber in a third partially straightened position 730 to an optic fiber in a fully straightened position 740. Illustratively, a rotation of actuation control 100 within handle inner portion 240 may be configured to extend cable 410 relative to flexible housing tube 400. In one or more embodiments, an extension of cable 410 relative to flexible housing tube 400 may be configured to reduce a force applied to flexible housing tube 400. Illustratively, a reduction of a force applied to a portion of flexible housing tube 400 may be configured to decompress a portion of flexible housing tube 400. In one or more embodiments, a decompression of a portion of flexible housing tube 400 may be configured to gradually straighten flexible housing tube 400. Illustratively, a gradual straightening of flexible housing tube 400 may be configured to gradually straighten optic fiber 450, e.g., from an optic fiber in a third partially straightened position 730 to an optic fiber in a fully straightened position 740. In one or more embodiments, a line tangent to optic fiber distal end 451 may be parallel to a line tangent to flexible housing tube proximal end 402, e.g., when optic fiber 450 comprises an optic fiber in a fully straightened position 740.

Illustratively, a surgeon may aim optic fiber distal end 451 at any of a plurality of targets within an eye, e.g., to perform a photocoagulation procedure, to illuminate a surgical target site, etc. In one or more embodiments, a surgeon may aim optic fiber distal end 451 at any target within a particular transverse plane of the inner eye by, e.g., rotating handle 300 to orient flexible housing tube 400 in an orientation configured to cause a curvature of flexible housing tube 400 within the particular transverse plane of the inner eye and varying an amount of rotation of actuation control 100 within handle inner portion 240. Illustratively, a surgeon may aim optic fiber distal end 451 at any target within a particular sagittal plane of the inner eye by, e.g., rotating handle 300 to orient flexible housing tube 400 in an orientation configured to cause a curvature of flexible housing tube 400 within the particular sagittal plane of the inner eye and varying an amount of rotation of actuation control 100 within handle inner portion 240. In one or more embodiments, a surgeon may aim optic fiber distal end 451 at any target within a particular frontal plane of the inner eye by, e.g., varying an amount of rotation of actuation control 100 within handle inner portion 240 to orient a line tangent to optic fiber distal end 451 wherein the line tangent to optic fiber distal end 451 is within the particular frontal plane of the inner eye and rotating handle 300. Illustratively, a surgeon may aim optic fiber distal end 451 at any target located outside of the particular transverse plane, the particular sagittal plane, and the particular frontal plane of the inner eye, e.g., by varying a rotational orientation of handle 300 and varying an amount of rotation of actuation control 100 within handle inner portion 240. In one or more embodiments, a surgeon may aim optic fiber distal end 451 at any target of a plurality of targets within an eye, e.g., without increasing a length of a portion of a steerable laser probe within the eye. Illustratively, a surgeon may aim optic fiber distal end 451 at any target of a plurality of targets within an eye, e.g., without decreasing a length of a portion of a steerable laser probe within the eye.

The foregoing description has been directed to particular embodiments of this invention. It will be apparent; however, that other variations and modifications may be made to the described embodiments, with the attainment of some or all of their advantages. Specifically, it should be noted that the principles of the present invention may be implemented in any system. Furthermore, while this description has been written in terms of a surgical instrument, the teachings of the present invention are equally suitable to any systems where the functionality may be employed. Therefore, it is the object of the appended claims to cover all such variations and modifications as come within the true spirit and scope of the invention.

What is claimed is:

1. A method comprising:
applying a first force vector to an actuation control anterior end of an actuation control of a handle;
directing the first force vector towards a handle distal end of the handle and away from a handle proximal end of the handle;
rotating the actuation control within an actuation control mount of the handle in a first direction until the actuation control is in a first desired rotational position within an inner portion of the handle;
preventing the actuation control from contacting an optic fiber due to a rotation of the actuation control by a geometry of an actuation chamber disposed in the actuation control, the actuation chamber extending completely from an actuation control distal end to an actuation control proximal end wherein the optic fiber has an optic fiber distal end and an optic fiber proximal end and wherein the optic fiber is disposed within the actuation chamber of the actuation control;
curving a flexible housing tube wherein the flexible housing tube has a flexible housing tube distal end and a flexible housing tube proximal end and wherein the optic fiber is disposed in the flexible housing tube wherein the optic fiber distal end is adjacent to the flexible housing tube distal end;
curving the optic fiber to a first curved position relative to the flexible housing tube proximal end;
removing the first force vector from the actuation control anterior end;
fixing the actuation control in the first desired rotational position within the inner portion of the handle;
fixing the optic fiber in the first curved position relative to the flexible housing tube proximal end;
aiming the optic fiber distal end at a surgical target within an eye; and
performing a photocoagulation procedure.

2. The method of claim 1 further comprising:
curving the optic fiber at least 45 degrees relative to the flexible housing tube proximal end.

3. The method of claim 2 further comprising:
curving the optic fiber at least 90 degrees relative to the flexible housing tube proximal end.

4. The method of claim 1 further comprising:
inserting the flexible housing tube in a cannula.

5. The method of claim 4 further comprising:
curving the optic fiber within an eye without increasing a length of the optic fiber within the eye.

6. The method of claim 4 further comprising:
curving the optic fiber within an eye without decreasing a length of the optic fiber within the eye.

7. The method of claim 1 further comprising:
rotating the actuation control within the actuation control mount of the handle in the first direction until the actuation control is in a second desired rotational position within the inner portion of the handle.

8. The method of claim 7 further comprising:
curving the optic fiber to a second curved position relative to the flexible housing tube proximal end wherein the second curved position relative to the flexible housing tube proximal end is greater than the first curved position relative to the flexible housing tube proximal end.

9. The method of claim 8 further comprising:
fixing the actuation control in the second desired rotational position within the inner portion of the handle.

10. The method of claim 9 further comprising:
fixing the optic fiber in the second curved position relative to the flexible housing tube proximal end.

11. The method of claim 10 further comprising:
curving the optic fiber at least 45 degrees relative to the flexible housing tube proximal end.

12. The method of claim 11 further comprising:
curving the optic fiber at least 90 degrees relative to the flexible housing tube proximal end.

13. The method of claim 1 further comprising:
applying a second force vector to the actuation control anterior end.

14. The method of claim 13 further comprising:
directing the second force vector towards the handle proximal end and away from the handle distal end.

15. The method of claim 14 further comprising:
rotating the actuation control within the actuation control mount of the handle in a second direction until the actuation control is in a second desired rotational position within the inner portion of the handle.

16. The method of claim 15 further comprising:
straightening the optic fiber to a straightened position relative to the flexible housing tube proximal end.

17. The method of claim 16 further comprising:
fixing the actuation control in the second desired rotational position within the inner portion of the handle.

18. The method of claim 17 further comprising:
fixing the optic fiber in the straightened position relative to the flexible housing tube proximal end.

* * * * *